United States Patent
Nakagawa et al.

(10) Patent No.: US 10,163,218 B2
(45) Date of Patent: Dec. 25, 2018

(54) IMAGE ANALYSIS DEVICE, IMAGE ANALYSIS METHOD, IMAGE ANALYSIS PROGRAM, CELL MANUFACTURING METHOD, CELL CULTURING METHOD, AND CELL MANUFACTURING DEVICE

(71) Applicant: NIKON CORPORATION, Tokyo (JP)

(72) Inventors: Kei Nakagawa, Fujisawa (JP);
Masafumi Mimura, Ageo (JP);
Takayuki Uozumi, Machida (JP)

(73) Assignee: NIKON CORPORATION, Tokyo (JP)

( * ) Notice: Subject to any disclaimer, the term of this patent is extended or adjusted under 35 U.S.C. 154(b) by 41 days.

(21) Appl. No.: 15/022,806

(22) PCT Filed: Sep. 12, 2014

(86) PCT No.: PCT/JP2014/074268
§ 371 (c)(1),
(2) Date: Mar. 17, 2016

(87) PCT Pub. No.: WO2015/041177
PCT Pub. Date: Mar. 26, 2015

(65) Prior Publication Data
US 2016/0232682 A1    Aug. 11, 2016

(30) Foreign Application Priority Data

Sep. 18, 2013  (JP) .................... 2013-193520
Sep. 18, 2013  (JP) .................... 2013-193545

(51) Int. Cl.
*G06K 9/00*      (2006.01)
*G06T 7/20*      (2017.01)
(Continued)

(52) U.S. Cl.
CPC .......... *G06T 7/2033* (2013.01); *C12M 41/14* (2013.01); *C12M 41/36* (2013.01); *C12N 5/0657* (2013.01);
(Continued)

(58) Field of Classification Search
None
See application file for complete search history.

(56) References Cited

U.S. PATENT DOCUMENTS 6,005,625 A    12/1999  Yokoyama
6,304,602 B1   10/2001  Yokoyama
(Continued)

FOREIGN PATENT DOCUMENTS

EP    2 463 379 A1   6/2012
JP    H08-063601     3/1996
(Continued)

OTHER PUBLICATIONS

May 16, 2017 Office Action issued in Japanese Patent Application No. 2015-537905.
(Continued)

*Primary Examiner* — Atiba O Fitzpatrick
(74) *Attorney, Agent, or Firm* — Oliff PLC

(57) ABSTRACT

An image analysis device includes a first calculating part that calculates a magnitude of motion of an image element from time-series images of pulsating myocardial cells, a second calculating part that calculates a feature quantity on the basis of the magnitude of the motion of the image element calculated by the first calculating part, and an identifying part that identifies whether the image element is a predetermined image element on the basis of the feature quantity calculated by the second calculating part.

6 Claims, 16 Drawing Sheets

(51) Int. Cl.
| | | |
|---|---|---|
| *C12M 1/00* | (2006.01) | |
| *C12M 1/34* | (2006.01) | |
| *C12N 5/077* | (2010.01) | |
| *G01N 33/483* | (2006.01) | |
| *G06T 7/00* | (2017.01) | |
| *G06T 7/215* | (2017.01) | |
| *G06T 7/246* | (2017.01) | |

(52) U.S. Cl.
CPC ....... *G01N 33/4833* (2013.01); *G06T 7/0012* (2013.01); *G06T 7/215* (2017.01); *G06T 7/246* (2017.01); *G06T 2207/30024* (2013.01)

(56) References Cited

U.S. PATENT DOCUMENTS

| | | | | |
|---|---|---|---|---|
| 2008/0304732 | A1* | 12/2008 | Rittscher | A61B 5/1105 382/133 |
| 2012/0122143 | A1 | 5/2012 | Mimura et al. | |
| 2013/0070971 | A1* | 3/2013 | Kunihiro | G06K 9/4642 382/107 |
| 2014/0226069 | A1 | 8/2014 | Oshima et al. | |

FOREIGN PATENT DOCUMENTS

| | | |
|---|---|---|
| JP | 2000-194865 A | 7/2000 |
| JP | 2005-293367 A | 10/2005 |
| JP | 2007-101867 A | 4/2007 |
| JP | 2010-538603 A | 12/2010 |
| JP | 2014-179061 A | 9/2014 |
| WO | 2008/149055 A1 | 12/2008 |
| WO | 2011/013319 A1 | 2/2011 |
| WO | 2011/122200 A1 | 10/2011 |

OTHER PUBLICATIONS

Loncaric, Sven et al., "Optical Flow Algorithm for Cardiac Motion Estimation", Annual Conference of the IEEE Engineering in Medicine and Biology Society, 2000, 22nd, vol. 1, pp. 415-417.

Kamgoué, A. et al., "Quantification of Cardiomyocyte Contraction Based on Image Correlation Analysis", Cytometry. Part A: The Journal of the International Society for Advancement of Cytometry, 2009, vol. 75, pp. 298-308.

Yokota, Arimitsu et al., "Estimation of Earthquake Motion by Image Analysis of Sliding Movement", ITE Technical Report, Jun. 26, 2006 (Jun. 26, 2006), vol. 30, No. 32, pp. 9-12.

Dec. 9, 2014 Search Report issued in International Patent Application No. PCT/JP2014/074268.

Dec. 9, 2014 Written Opinion issued in International Patent Application No. PCT/JP2014/074268.

* cited by examiner

IMAGE ANALYSIS DEVICE, IMAGE ANALYSIS METHOD, IMAGE ANALYSIS PROGRAM, CELL MANUFACTURING METHOD, CELL CULTURING METHOD, AND CELL MANUFACTURING DEVICE

TECHNICAL FIELD

The present invention relates to an image analysis device, an image analysis method, an image analysis program, a cell manufacturing method, a cell culturing method, and a cell manufacturing device.

Priority is claimed on Japanese Patent Application No. 2013-193545, filed Sep. 18, 2013 and Japanese Patent Application No. 2013-193520, filed Sep. 18, 2013, the content of which is incorporated herein by reference.

BACKGROUND

In recent years, attempts to use stem cells for regenerative medicine and drug development have been made. Because the stem cells have both pluripotency and proliferation potency, any cell can be theoretically manufactured in any amount. As an application example of this technology, there is culturing of myocardial cells. Because myocardial cells are terminally differentiated cells, it is difficult to regenerate myocardial cells that are injured due to ischemic heart disease or the like. Thus, a treatment method of differentiating stem cells into myocardial cells and transplanting the obtained myocardial cells into the heart is considered.

However, the number of cells to be differentiated into objective cells is not necessarily large even when differentiation induction is performed on the stem cells. Thus, when wanting to use cells after differentiation, it is necessary to identify and separate differentiated cells and undifferentiated cells. When an actual application is considered, it is preferable to automatically perform a process of selecting the cells in terms of safety assurance and manufacturing efficiency. Also, it is preferable to perform a non-invasive technique so that the differentiated cells are not injured.

There is technology for tracking the motion of an object within an image as one of technologies for analyzing time-series images. Technology for measuring the pulsations of a heart or myocardial cells from an image in which the heart and the myocardial cells are observed in time series by applying the above-described technology is disclosed in Non Patent Document 1 and Non Patent Document 2. Cultured myocardial cells are characterized in that autonomous pulsation is performed. Therefore, it is possible to identify the myocardial cells differentiated from the stem cells automatically and non-invasively by employing the above-described technologies and the characteristic of the cultured myocardial cells.

RELATED ART DOCUMENTS

Non Patent Documents

Non Patent Document: S. Loncaric, Z. Majcenic "Optical flow algorithm for cardiac motion estimation," Annual Conference of the IEEE Engineering in Medicine and Biology Society, 2000, 22nd, Vol. 1, pp. 415-417

Non Patent Document 2: A. Kamgue, J. Ohayon, Y. Usson, L. Riou, P. Tracqui "Quantification of cardiomyocyte contraction based on image correlation analysis," Cytometry. Part A: The Journal of the International Society for Advancement of Cytometry 2009, Vol. 75, pp. 298-308

SUMMARY OF INVENTION

Problems to be Solved by the Invention

However, in the conventional technology, the motions of other image elements within an observation image in addition to the pulsations of myocardial cells may be recognized as the pulsations of the myocardial cells, and an image element which performs autonomous motions like the pulsations of the myocardial cells and other image elements may not be accurately identified.

Also, in the conventional technology, the motion of one myocardial cell may be separated into a plurality of small regions and detected, or conversely a plurality of myocardial cells may be detected as one region. That is, image elements obtained by imaging the same myocardial cell (motion object) may not be accurately grouped.

According to an aspect of the present invention, an objective of the invention is to more accurately identify image elements which perform autonomous motion from a time-series image.

Also, according to another aspect of the present invention, an objective of the invention is to more accurately group image elements in one group in which the same motion object is likely to be imaged.

Means for Solving the Problem

An image analysis device of an aspect of the present invention is an image analysis device including a first calculating part that calculates a magnitude of motion of an image element from time-series images of pulsating myocardial cells; a second calculating part that calculates a feature quantity on the basis of the magnitude of the motion of the image element calculated by the first calculating part; and an identifying part that identifies whether the image element is a predetermined image element on the basis of the feature quantity calculated by the second calculating part.

Also, an image analysis method of an aspect of the present invention is an image analysis method including computing, by a computer, a magnitude of motion of an image element from time-series images of pulsating myocardial cells; computing, by the computer, a feature quantity on the basis of the calculated magnitude of the motion of the image element; and identifying, by the computer, whether the image element is a predetermined image element on the basis of the calculated feature quantity.

Also, an image analysis program of an aspect of the present invention is an image analysis program for causing a computer to calculate a magnitude of motion of an image element from time-series images of pulsating myocardial cells; calculate a feature quantity on the basis of the calculated magnitude of the motion of the image element; and identify whether the image element is a predetermined image element on the basis of the calculated feature quantity.

Also, a cell manufacturing method of an aspect of the present invention is a cell manufacturing method including a cell culturing procedure of culturing cells; an imaging procedure of imaging the cells cultured in the culturing procedure a plurality of times; a first calculating procedure of calculating a magnitude of motion of an image element included in a plurality of images captured in the imaging procedure; a second calculating procedure of calculating a feature quantity on the basis of the magnitude of the motion of the image element calculated in the first calculating procedure; and an identifying procedure of identifying whether the image element is a desired cell on the basis of the feature quantity calculated in the second calculating procedure.

Also, a cell culturing method of an aspect of the present invention is a cell culturing method including a cell culturing procedure of culturing cells; an imaging procedure of imaging the cells cultured in the culturing procedure a plurality of times; a first calculating procedure of calculating a magnitude of motion of an image element included in a plurality of images captured in the imaging procedure; a second calculating procedure of calculating a feature quantity on the basis of the magnitude of the motion of the image element calculated in the first calculating procedure; an identifying procedure of identifying whether the image element is a desired cell on the basis of the feature quantity calculated in the second calculating procedure; a cell acquiring procedure of removing the identified desired cell or a cell other than the desired cell, and an acquired cell culturing procedure of further culturing the desired cell acquired in the cell acquiring procedure.

Also, a cell manufacturing device of an aspect of the present invention is a cell manufacturing device including a cell culturing part that cultures cells; an imaging part that images the cells cultured by the culturing part a plurality of times; a first calculating part that calculates a magnitude of motion of an image element included in a plurality of images captured by the imaging part; a second calculating part that calculates a feature quantity on the basis of the magnitude of the motion of the image element calculated by the first calculating part; an identifying part that identifies whether the image element is a desired cell on the basis of the feature quantity calculated by the second calculating part; and an extracting part that extracts the cell corresponding to the image element identified to be the desired cell by the identifying part.

Also, an image analysis device of an aspect of the present invention is an image analysis device including a calculating part that calculates a feature quantity related to motion of each image element from time-series images obtained by imaging an observation target including one or more motion objects in time series; and a grouping part that groups image elements similar in the feature quantity calculated by the calculating part as candidates for image elements of one group obtained by imaging the same motion object.

Also, an image analysis method of an aspect of the present invention is an image analysis method including calculating, by a computer, a feature quantity related to motion of each image element from time-series images obtained by imaging an observation target including one or more motion objects in time series; and estimating, by the computer, that image elements similar in the calculated feature quantity are image elements obtained by imaging the same motion object and grouping the image elements.

Also, an image analysis program of an aspect of the present invention is an image analysis program for causing a computer to calculate a feature quantity related to motion of each image element from time-series images obtained by imaging an observation target including one or more motion objects in time series; and estimate that image elements similar in the calculated feature quantity are image elements obtained by imaging the same motion object and group the image elements.

Also, a cell manufacturing method of an aspect of the present invention is a cell manufacturing method including a cell culturing procedure of culturing cells; an imaging procedure of imaging the cells cultured in the culturing procedure a plurality of times; a calculating procedure of calculating a feature quantity related to motion of each image element from a plurality of captured images; a grouping procedure of estimating that image elements similar in the calculated feature quantity are image elements obtained by imaging the same cell and grouping the image elements; and an identifying procedure of identifying whether the grouped image elements are desired cells.

Also, a cell manufacturing device of an aspect of the present invention is a cell manufacturing device including a cell culturing part that cultures cells; an imaging part that images the cells cultured by the culturing part a plurality of times; a calculating part that calculates a feature quantity related to motion of each image element from a plurality of images captured by the imaging part; a grouping part that estimates that image elements similar in the feature quantity calculated by the calculating part are image elements obtained by imaging the same cell and group the image elements; an identifying part that identifies whether the image elements grouped by the grouping part show desired cells; and an extracting part that extracts cells corresponding to the image elements identified to show the desired cells by the identifying part.

Advantage of the Invention

According to an aspect of the present invention, it is possible to more accurately identify image elements which perform autonomous motion from a time-series image.

Also, according to another aspect of the present invention, it is possible to more accurately group image elements in one group in which the same motion object is likely to be imaged.

DESCRIPTION OF THE EMBODIMENTS

Hereinafter, embodiments of an image analysis device, an image analysis method, an image analysis program, a cell manufacturing method, a cell culturing method, and a cell manufacturing device of the present invention will be described with reference to the drawings.

First Embodiment

[Configuration of Incubator]

Figure 1:
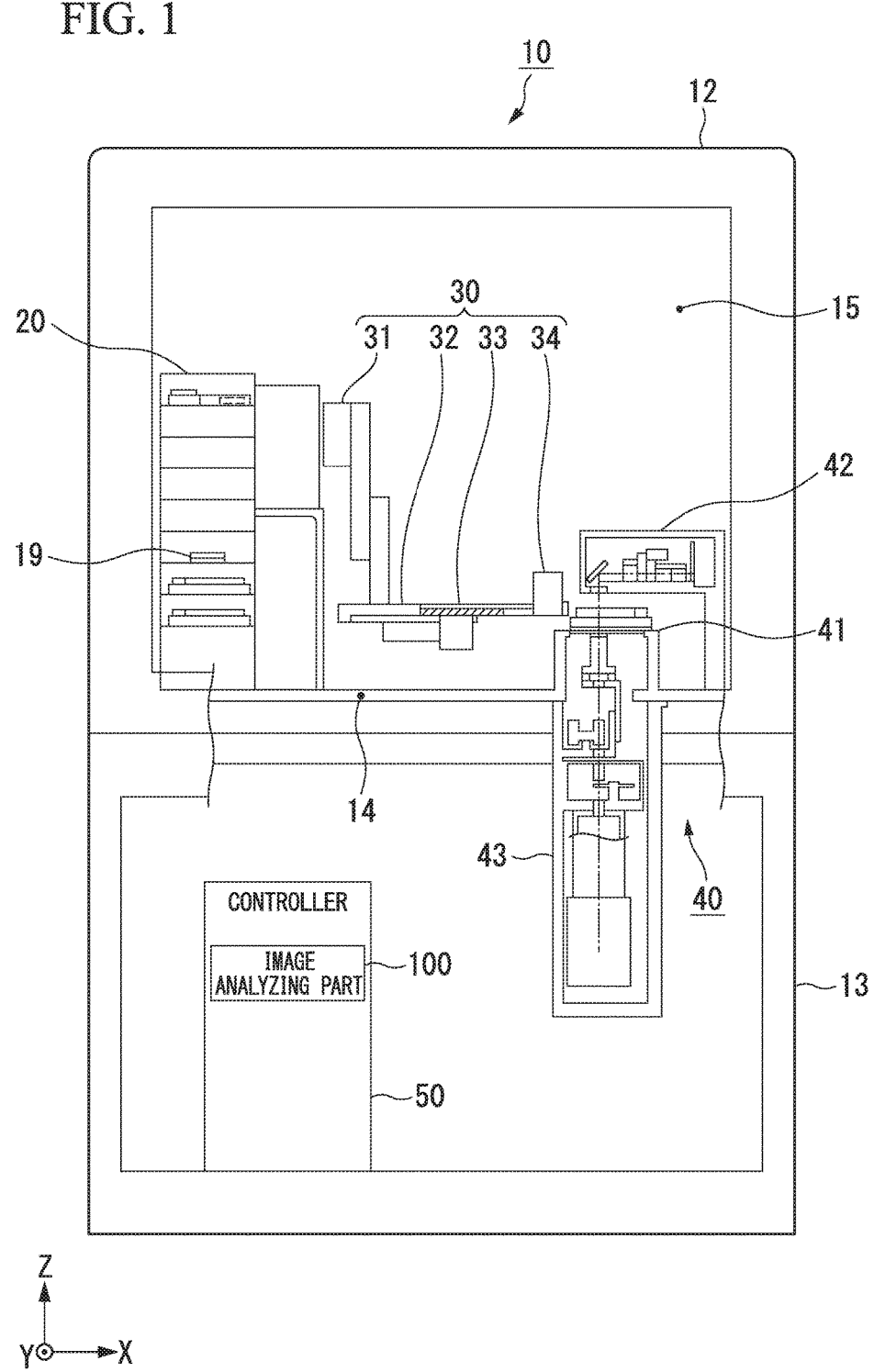
FIG. 1 is an example of a perspective view of an incubator including an image analyzing part (an image analysis device) viewed from the front.
Figure 2:
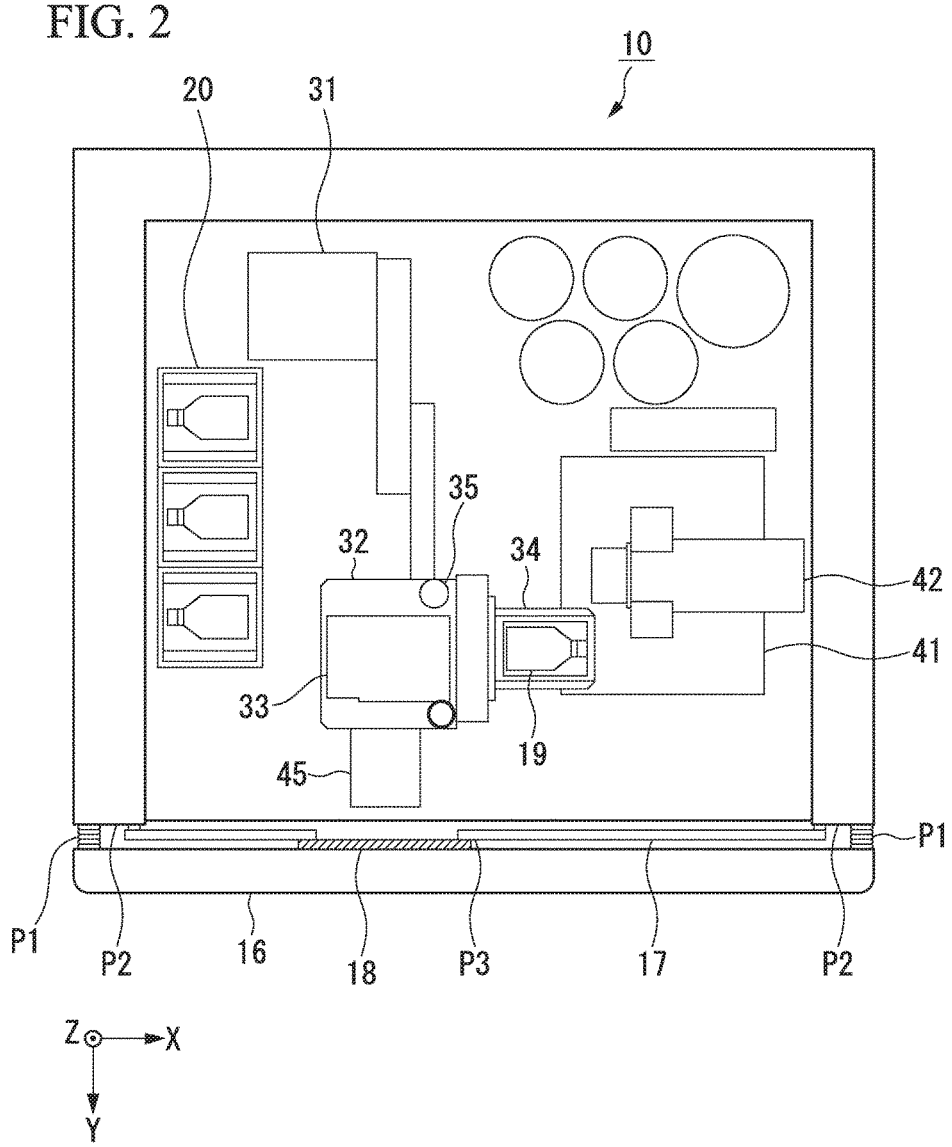
FIG. 2 is an example of a perspective view of the incubator viewed from the top.

FIG. 1 is an example of a perspective view of an incubator 10 including an image analyzing part (an image analysis device) viewed from the front (a +Y direction in the drawing). Also, FIG. 2 is an example of a perspective view of the incubator 10 viewed from the top (a +Z direction in the drawing). In FIGS. 1 and 2, a positional relationship is illustrated using a mutually orthogonal XYZ coordinate system.

The incubator 10 includes an upper casing 12 and a lower casing 13. The upper casing 12 is arranged on the lower casing 13. Also, internal spaces of the upper casing 12 and the lower casing 13 are partitioned into a top and bottom space by a base plate 14.

First, an overview of a configuration of the upper casing 12 will be described. A thermostatic chamber 15 for culturing cells is formed inside the upper casing 12. The thermostatic chamber 15 has a temperature adjusting part and a humidity adjusting part (not illustrated), and an environment (for example, an atmosphere of a temperature of 37° C. and a humidity of 90%) suitable for culturing cells is maintained within the thermostatic chamber 15.

A large door 16, a medium door 17, and a small door 18 are arranged on a front surface of the thermostatic chamber 15. The large door 16 covers front surfaces of the upper casing 12 and the lower casing 13. The medium door 17 covers the front surface of the upper casing 12 and isolates environments of the thermostatic chamber 15 from the outside when the large door 16 is open. The small door 18 is a door for loading and unloading a culturing container 19 that cultures cells, and is attached to the medium door 17. It is possible to suppress a change in the environment of the thermostatic chamber 15 by loading and unloading the culturing container 19 by the small door 18. Also, the airtightness of the large door 16, the medium door 17, and the small door 18 is maintained by packings P1, P2, and P3 respectively. Also, a stocker 20, a container transporting part 30, an observation unit 40, and a mounting table 45 are arranged in the thermostatic chamber 15. The mounting table 45 is arranged near the small door 18 and the culturing container 19 is loaded and unloaded via the small door 18.

The stocker 20 is arranged on the left side of the thermostatic chamber 15 when viewed from the front surface (+Y direction) of the upper casing 12. The stocker 20 has a plurality of shelves and can store a plurality of culturing containers 19 on each shelf of the stocker 20. Each culturing container 19 stores stem cells serving as a culturing target with a culture medium. Also, differentiation induction for myocardial cells is performed on the stem cells, and some cells are differentiated into myocardial cells. The cells differentiated into myocardial cells perform autonomous pulsation.

The container transporting part 30 is arranged at the center of the thermostatic chamber 15 when viewed from the front surface of the upper casing 12. The container transporting part 30 transports the culturing container 19 from the stocker 20 to a sample stage 41 of the observation unit 40, transports the culturing container 19 from the mounting table 45 to the stocker 20 or the observation unit 40, or transports the culturing container 19 from the sample stage 41 of the observation unit 40 to the stocker 20.

The container transporting part 30 has a vertical robot 31 having an articulated arm, a rotary stage 32, a mini-stage 33, and an arm part 34. The rotary stage 32 is attached to a tip part of the vertical robot 31 so that the rotary stage 32 is rotatable by 180 degrees in a horizontal direction (X-Y horizontal direction) around a rotary shaft 35. Thus, the rotary stage 32 can cause the arm part 34 to be opposite to the stocker 20, the sample stage 41 and the mounting table 45. The mini-stage 33 is attached to the rotary stage 32 so that the mini-stage 33 can slide in the horizontal direction. The arm part 34 for holding the culturing container 19 is attached to the mini-stage 33.

The observation unit 40 is arranged on the right side of the thermostatic chamber 15 when viewed from the front surface of the upper casing 12. The observation unit 40 can capture and observe an image of cells within the culturing container 19 for each predetermined time interval. Hereinafter, this observation is also referred to as a "time-lapse observation."

The observation unit 40 is arranged to be fitted into an opening part of the base plate 14 of the upper casing 12. The observation unit 40 includes the sample stage 41, a stand arm 42 extending to an upper side of the sample stage 41, and a main body part 43 in which a microscope optical system for phase difference observation and an imaging part 160 (to be described below) are embedded. While the sample stage 41 and the stand arm 42 are arranged in the thermostatic chamber 15, the main body part 43 is stored inside the lower casing 13.

The sample stage 41 is constituted of a transparent material and the culturing container 19 can be placed on the sample stage 41. This sample stage 41 is configured to be movable in the horizontal direction and can adjust a position of the culturing container 19 placed in its upper surface. Also, a light-emitting diode (LED) light source is embedded in the stand arm 42. The imaging part 160 can acquire a microscope image of cells by imaging cells of the culturing container 19 transmissively illuminated from the upper side of the sample stage 41 by the stand arm 42 via the microscope optical system.

Next, an overview of a configuration of the lower casing 13 will be described. The main body part 43 and a controller 50 of the incubator 10 are stored inside the lower casing 13. The controller 50 includes a processor such as a central processing unit (CPU), a hard disk drive (HDD), a storage 150 (to be described below) such as a flash memory, a random access memory (RAM), a read only memory (ROM), etc. Management data related to each culturing container 19 stored in the stocker 20, data of a microscope image captured by the imaging part 160, etc. are stored in the storage 150. Also, a processing result of image processing, temporary data generated during the processing, and a program to be executed by the CPU are stored in the storage 150.

Also, index data which is identification information of an individual culturing container 19, a storage position of the culturing container 19 in the stocker 20, the type and shape (a well plate, a dish, a flask, or the like) of the culturing container 19, the type of cells cultured in the culturing container 19, an observation schedule of the culturing container 19, imaging conditions (a magnification of an objective lens, an observation point within the container, etc.) during time-lapse observation, etc. are included in the above-described management data. Also, management data for each small container may be generated for the culturing container 19 capable of simultaneously culturing cells in a plurality of small containers such as well plates.

The controller 50 is connected to the temperature adjusting part, the humidity adjusting part, the container transporting part 30, and the observation unit 40. The controller 50 generally controls each part of the incubator 10 according to a predetermined program. As an example, the controller 50 maintains predetermined environmental conditions within the thermostatic chamber 15 by controlling each of the temperature adjusting part and the humidity adjusting part. Also, the controller 50 executes time-lapse observation of cells within the culturing container 19 by controlling the container transporting part 30 and the observation unit 40 on the basis of a predetermined observation schedule. Further, an image analyzing part 100 of the controller 50 analyzes time-series images acquired in time-lapse observation and identifies autonomously pulsating myocardial cells.

[Configuration of Image Analyzing Part]

Figure 3:
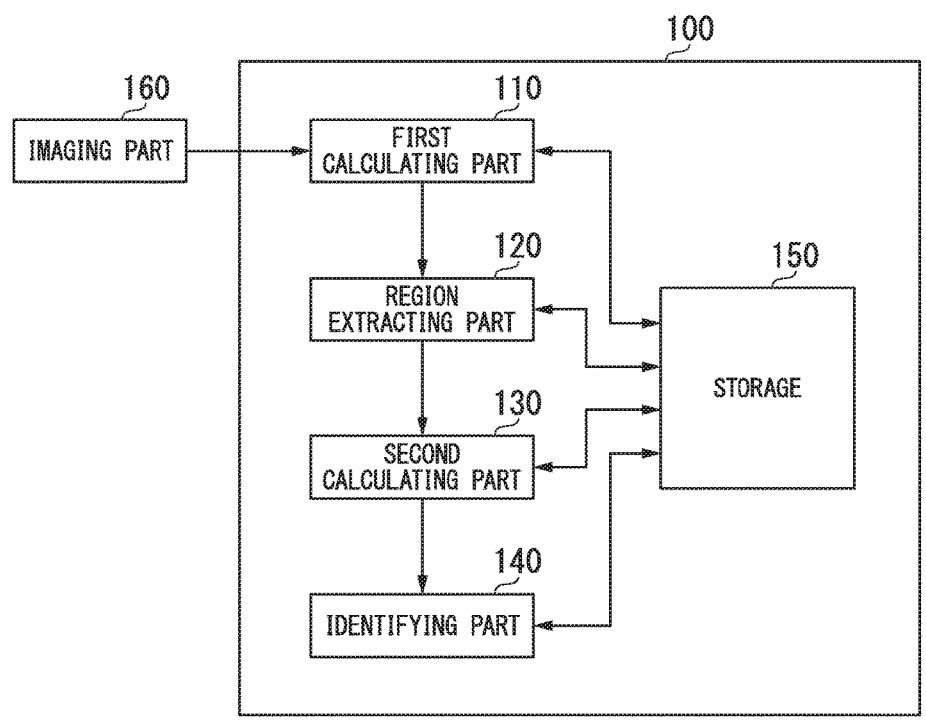
FIG. 3 is a diagram illustrating an example of a functional configuration of an image analyzing part according to a first embodiment.

Hereinafter, identification of myocardial cells which perform autonomous pulsation will be described. FIG. 3 is a diagram illustrating an example of a functional configuration of the image analyzing part 100 according to the first embodiment. The image analyzing part 100 includes, for example, a first calculating part 110, a region extracting part 120, a second calculating part 130, an identifying part 140, and the storage 150. These functional parts are, for example, software function parts which function by executing a program stored in the storage 150 by the CPU of the controller 50. Also, some or all of these functional parts may be hardware function parts such as large scale integration (LSI) and an application specific integrated circuit (ASIC). Also, although the image analyzing part 100 is illustrated to be one function of the controller 50 in FIG. 1, the image analyzing part 100 (the image analysis device) may be implemented by a computer independent from the incubator 10.

The imaging part 160 iteratively images the cultured myocardial cells in a predetermined cycle. Here, the magnification of the objective lens of the microscope optical system of the observation unit 40 is 2× and the numerical aperture is 0.09. Also, the imaging part 160 performs imaging at a resolution of 1000×1000 pixels. Because the magnification of the objective lens of the microscope optical system of the observation unit 40 is 2×, the imaging part 160 can image cells of a wide range in one imaging operation. Thus, even when there are a few pulsating cells differentiated into myocardial cells, the image analyzing part 100 can efficiently find the cells. Also, the above-described observation conditions are an example, but this embodiment is not limited to the above-described observation conditions and is applicable to other observation conditions. Also, the imaging part 160 outputs the captured time-series image to the first calculating part 110.

The first calculating part 110 extracts, for example, a plurality of sets of temporally adjacent (every one or every two, etc.) images, among time-series images input from the imaging part 160, compares images of each set, and calculates a magnitude of motion for each pixel of the image (to be described below). The first calculating part 110 outputs the magnitude of the motion of each pixel for each calculated time-series image to the region extracting part 120.

The region extracting part 120 extracts a region in which there is motion within the image (hereinafter referred to as a "motion region") on the basis of the magnitude of the motion of each pixel for each time-series image input from the first calculating part 110. The region extracting part 120 outputs a set of identification information indicating each motion region and a magnitude of motion of the motion region to the second calculating part 130.

Here, the magnitude of the motion is associated with pixels considered to show the same position of the object, for example, between a certain image (image A) and an image (image B) immediately after the image A, and a distance from a corresponding pixel in the image A is obtained for each pixel of the image B. Association may be performed, for example, using a technique such as a known optical flow or a block matching method.

Because the magnitude of the motion is obtained for a set of temporally adjacent pixels among time-series images, a number which is 1 less than the number of frames of the time-series images is calculated.

The second calculating part 130 calculates, for example, a plurality of feature quantities from the magnitudes of the motions of the motion regions input from the region extracting part 120. The second calculating part 130 outputs the calculated feature quantities to the identifying part 140. The identifying part 140 identifies whether the motion of each motion region is pulsations of myocardial cells on the basis of the feature quantities input from the second calculating part 130. The identifying part 140 associates an identification result with the identification information of the motion result.

[Processing Flow]

Figure 4:
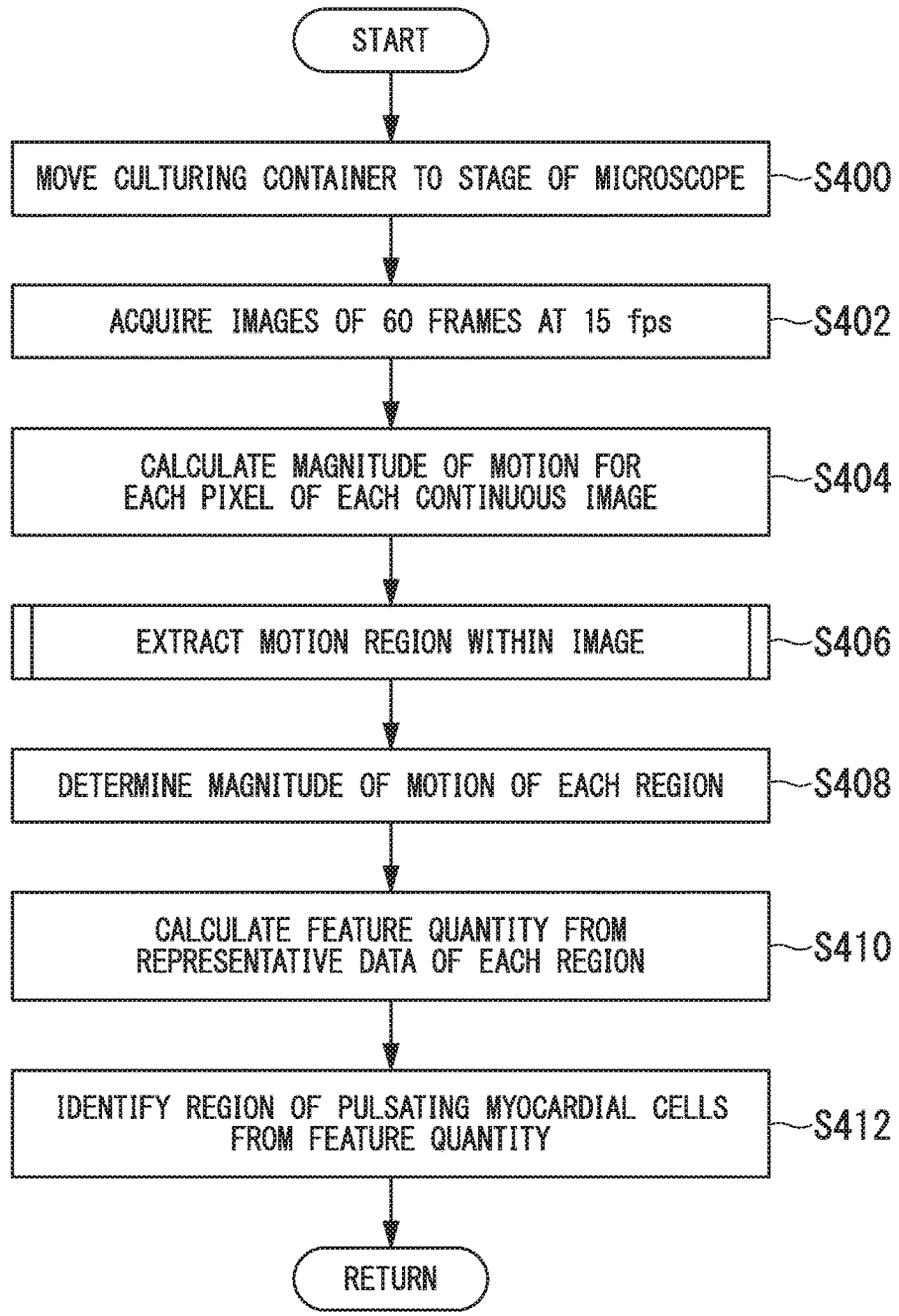
FIG. 4 is an example of a flowchart illustrating a flow of observation of cells, imaging, and image processing.

FIG. 4 is an example of a flowchart illustrating a flow of observation of cells, imaging, and image processing.

(Step S400) First, the controller 50 refers to an observation schedule within management data and outputs a transportation command of the culturing container 19 for which an observation time is reached to the container transporting part 30. The container transporting part 30 transports the culturing container 19 to the sample stage on the basis of the transportation command of the culturing container 19 input from the controller 50.

(Step S402) Next, the imaging part 160 images cells within the culturing container 19 in a predetermined cycle a plurality of times. The imaging part 160 acquires images at 15 fps (frames/second) for four seconds. In this case, time-series images obtained in one observation operation are 60 frames. The imaging part 160 outputs the captured time-series images of the cells to the first calculating part 110.

(Step S404) Next, the first calculating part 110 calculates the magnitude of the motion of pixels on the basis of a comparison of luminances of each pixel in the time-series image of cells input from the imaging part 160 and each pixel of an image immediately after the input image as described above. The first calculating part 110 outputs the calculated magnitude of the motion to the region extracting part 120.

(Step S406) Next, the region extracting part 120 extracts a motion region within the image on the basis of the magnitude of the motion input from the first calculating part 110. The motion region is a set of pixels having the magnitude of the motion greater than a reference (details will be described below). The region extracting part 120 allocates individual identification information to each extracted motion region and associates a coordinate group of pixels included in each motion region and identification information.

(Step S408) Next, the region extracting part 120 calculates a magnitude of motion of each motion region from magnitudes of motions of pixels belonging to each motion region. The region extracting part 120 outputs a set of the calculated magnitude of the motion of each motion region and the identification information of the motion region to the second calculating part 130.

(Step S410) Next, the second calculating part 130 calculates, for example, six feature quantities on the basis of the magnitude of the motion of each motion region. The six feature quantities are, for example, a maximum value of the magnitude of the motion, a degree of projection, time periodicity, the variance of a frequency spectrum, a ratio of high-frequency components to low-frequency components, and a ratio of intermediate-frequency components to the low-frequency components. Also, some of the six feature quantities may be omitted or other feature quantities may be calculated and used. The second calculating part 130 outputs a set of the six calculated feature quantities and the identification information of the motion region to the identifying part 140.

(Step S412) The identifying part 140 identifies whether each motion region shows the pulsations of myocardial cells on the basis of the six feature quantities input from the second calculating part 130.

Figure 5:
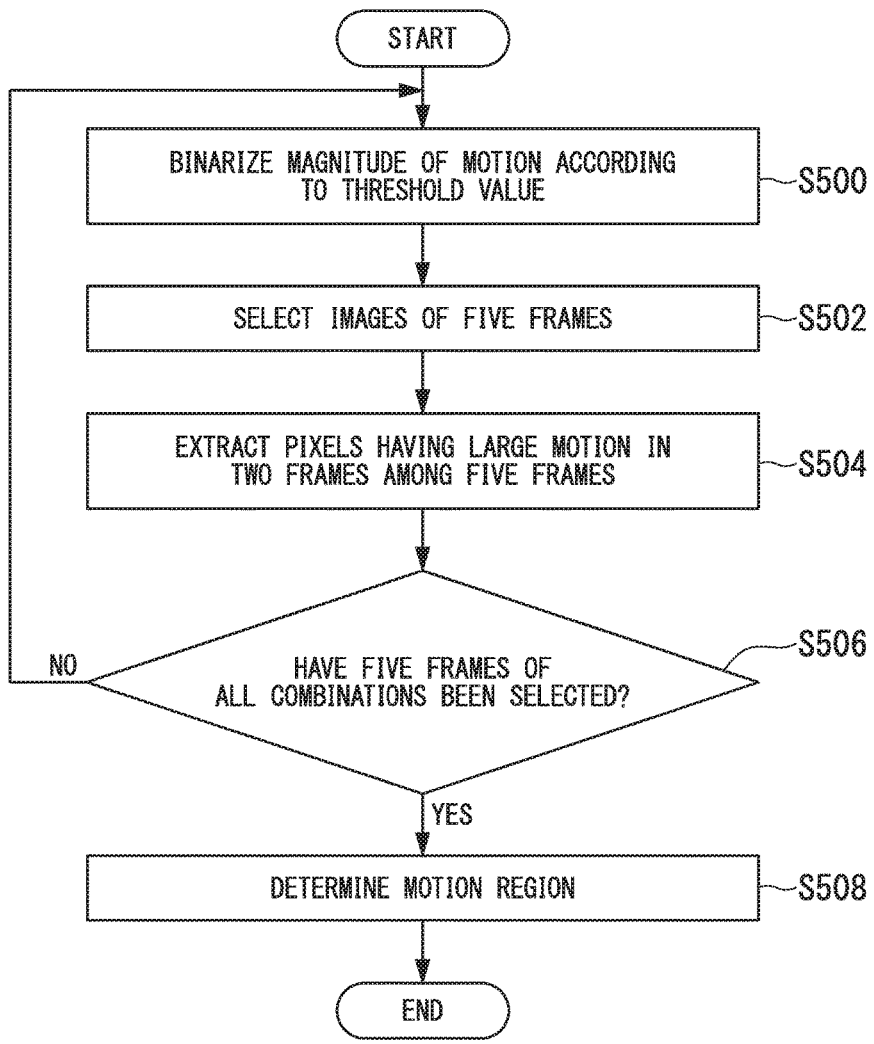
FIG. 5 is an example of a flowchart illustrating a flow of a process of extracting a motion region from a time-series image which is executed by a region extracting part according to the first embodiment.

Here, a process in which the region extracting part 120 extracts the motion region from the time-series image (the process of step S406 in FIG. 4) will be described. FIG. 5 is an example of a flowchart illustrating a flow of the process of extracting a motion region from a time-series image which is executed by the region extracting part 120 according to the first embodiment.

(Step S500) First, the region extracting part 120 compares a magnitude of motion of each pixel with a threshold value for each image of time-series images and divides the pixels into a pixel having large motion and a pixel having small motion by performing binarization to a magnitude greater than or equal to the threshold value and a magnitude less than the threshold value.

(Step S502) Next, the region extracting part 120 extracts images of five frames which are temporally successive among the time-series images. When the region extracting part 120 sets images for which magnitudes of motions are obtained among time-series images #0 to #59 for 60 frames to images #1 to #59, for example, images for five frames such as images #1 to #5 in a first time, images #2 to #6 in a second time, and images #3 to #7 in a third time are extracted (in contrast, images may be extracted in descending order). Also, the extraction of images for five frames from all the time-series images is only an example, and the region extracting part 120 may extract any number of images.

(Step S504) Next, the region extracting part 120 extracts pixels in which motion is large is determined in at least two frames among the images of the five extracted frames and causes the storage 150 to store the extracted pixels.

(Step S506) Next, the region extracting part 120 determines whether images of five frames of all combinations are extracted from the images #1 to #59. When the images of the five frames of all the combinations are extracted (YES), the region extracting part 120 transitions to step S508. When the images of the five frames of all the combination are not extracted (NO), the region extracting part 120 returns to step S500 and extracts images of the next five frames.

(Step S508) When the images of the five frames of all the combinations are extracted, the region extracting part 120 refers to all the pixels stored in the storage 150 in the process of step S502 of each routine and sets a region in which the pixels stored in the storage 150 are adjacent to each other as one motion region. The region extracting part 120 allocates individual identification information to each motion region and causes the storage 150 to store the individual identification information according to coordinates occupied by the above-described motion region.

Figure 6:
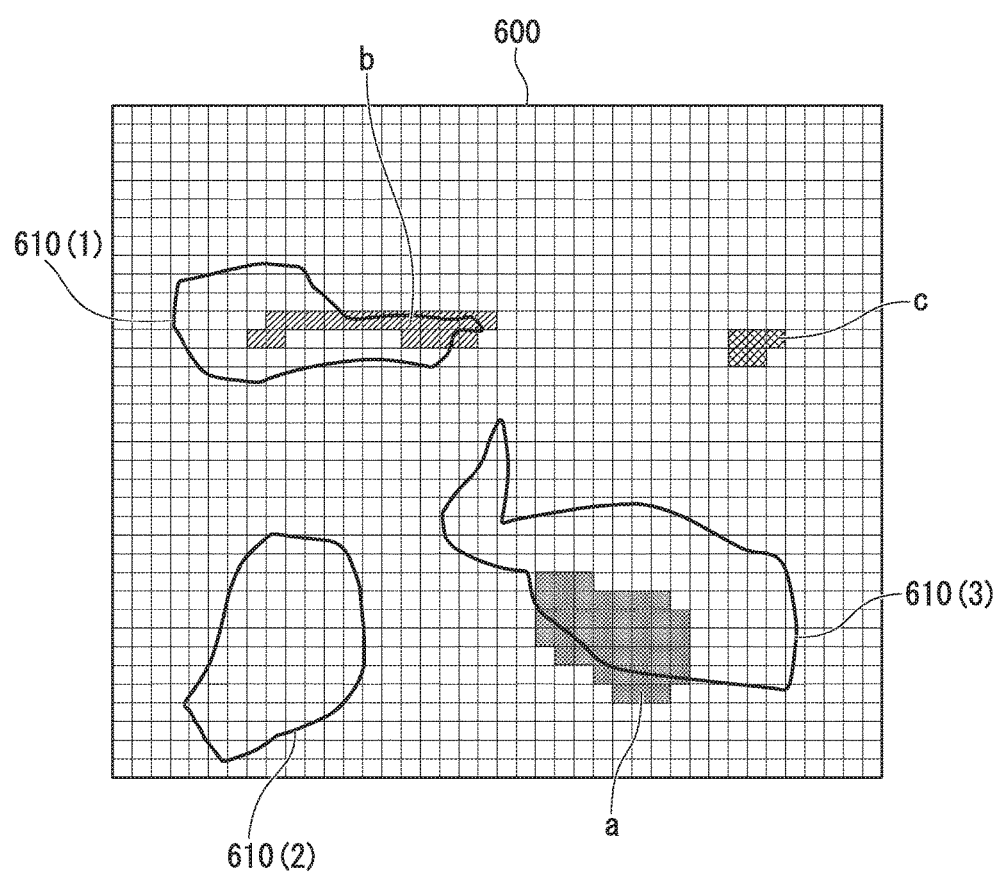
FIG. 6 is a diagram illustrating an example of cells included in a part of an image captured by an imaging part and motion regions extracted by the region extracting part from the image.

FIG. 6 is a diagram illustrating an example of cells 610(1) to 610(3) included in a part 600 of an image captured by the imaging part 160 and motion regions a to c extracted by the region extracting part 120 from the image. As the motion region, for example, three types of motion regions to be described below are extracted. A motion region a is a motion region from which motion is extracted on the basis of pulsations of myocardial cells. Hereinafter, this motion region is referred to as a "pulsation region." A motion region b is a motion region extracted due to a shaking of the culture fluid. Hereinafter, this motion region is referred to as a "shaking-of-liquid region." A motion region c is, for example, a motion region extracted due to a noise element. Hereinafter, this motion region is referred to as a "noise region."

Here, a method of calculating a magnitude of motion of each motion region (step S408 in FIG. 4) will be described in detail. As in the following, the region extracting part 120 confirms a magnitude of motion of each pixel within each motion region for all the time-series images. First, the region extracting part 120 extracts a pixel in which a magnitude of largest motion is shown among pixels within the motion region (a "pixel having largest motion within the region"). Next, the region extracting part 120 selects an image region of 5×5 pixels around the pixel having the largest motion within the region. The region extracting part 120 calculates an average value of magnitudes of motions of the selected image region of 5×5 pixels for all the time-series images. The region extracting part 120 outputs the calculated magnitude of the motion of each motion region to the second calculating part 130 in association with identification information of the corresponding motion region.

[Overview of Feature of Magnitude of Motion of Each Motion Region]

Figure 7:
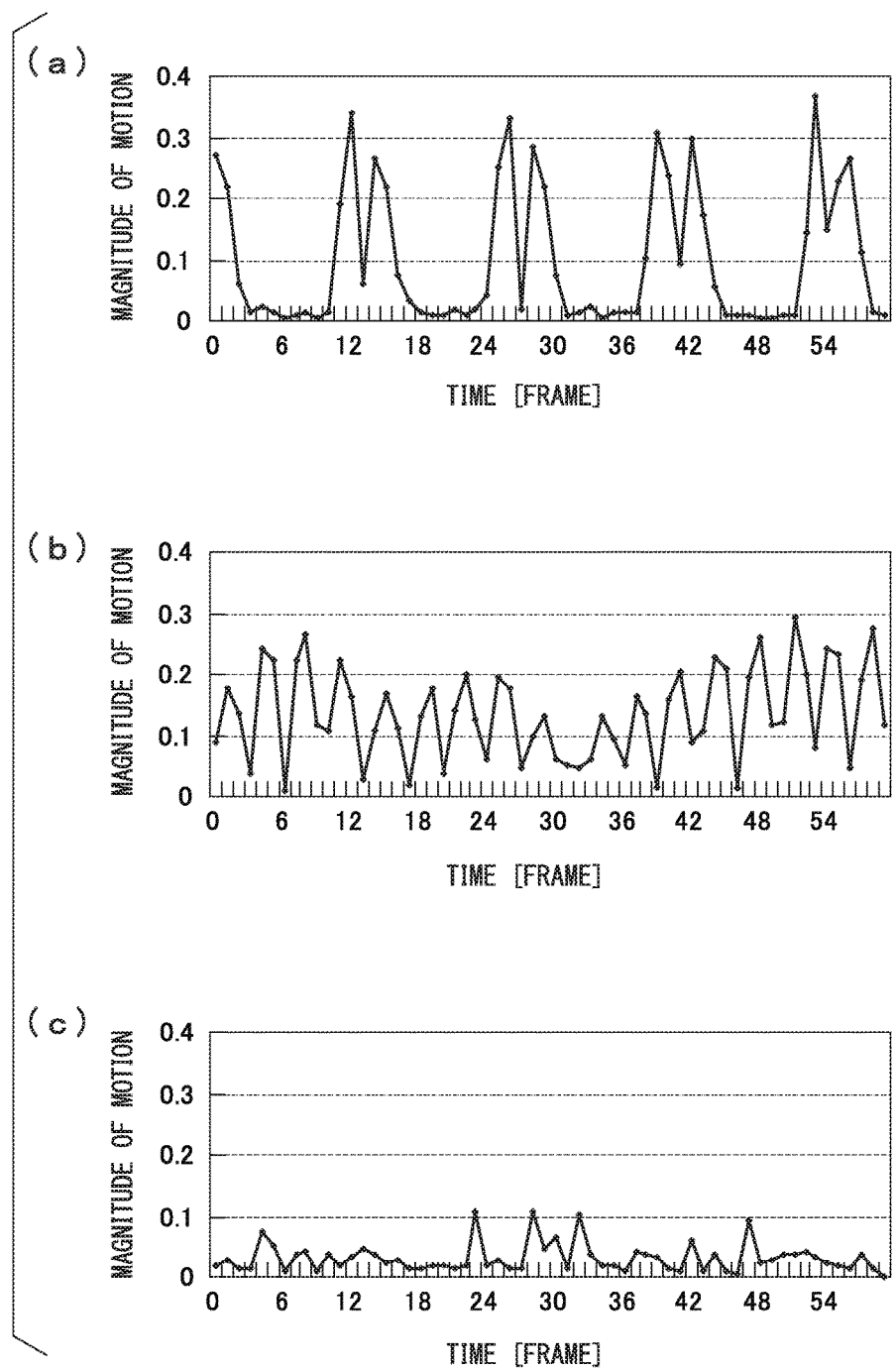
FIG. 7 is an example of a graph illustrating a change in a magnitude of a motion of each motion region extracted by the region extracting part.

Here, the feature of the magnitude of the motion of each motion region will be described. FIG. 7 is an example of a graph illustrating a change in a magnitude of each motion region extracted by the region extracting part 120. In the graph of FIG. 7, the horizontal axis represents a frame of a time-series image and the vertical axis represents a value of a magnitude of motion. Also, in FIG. 7, (a) illustrates a pulsation region, (b) illustrates a shaking-of-liquid region, and (c) illustrates a noise region.

In (a) pulsations of myocardial cells, an autonomous contraction (motion) state and a relaxation (stationary) state are iterated. Accordingly, as illustrated in FIG. 7(a), the magnitude of motion of the pulsation region becomes periodic. In a sampling condition of this embodiment, a time distribution from the beginning of the contraction of myocardial cells to the relaxation generally fits within 5 to 10 frames per time. On the other hand, a time in which the myocardial cells are stationary significantly differs according to the cell. In the myocardial cells, there are cells which iteratively contract in a short cycle substantially without a stationary time, and, for example, there are also cells which contract only once in the observation for four seconds.

(b) Shaking of the culture fluid is caused by an aftershock of the culture fluid within the culturing container 19 due to a vibration when the container transporting part 30 transports the culturing container 19 onto the sample stage 41. A cycle of the aftershock of the culture fluid is shorter than a cycle of pulsations of myocardial cells in most cases. Accordingly, a cycle of motion of a floating cell, a floating material, or the like moved by the aftershock of the culturing fluid is approximately shorter than the cycle of pulsations of the myocardial cells. As illustrated in FIG. 7(b), the magnitude of motion of the shaking-of-liquid region changes in a shorter cycle than that of the pulsation region.

(c) The noise region is a noise region in which noise occurring in a certain pixel of a certain frame and noise occurring in the vicinity of the pixel of a separate frame is extracted due to a wrong determination of motion of the same image element. Because the same image element does not actually move, the magnitude of the detected motion lacks temporal continuity. Accordingly, as illustrated in FIG. 7(c), the periodicity is rarely seen in the magnitude of the motion of the noise region in many cases.

As described above, the magnitude of the motion of the motion region has a characteristic according to a type of motion region. However, the magnitude of the motion of the motion region which is actually calculated has a large difference according to an individual motion region and it is difficult to identify a type of motion region in a single measure. Therefore, the image analyzing part 100 of this embodiment calculates a plurality of feature quantities based on the magnitude of the motion and generally identifies a type of motion region using the plurality of calculated feature quantities.

[Calculation of Feature Quantity]

The calculation of a feature quantity will be described in detail. In this embodiment, the second calculating part 130 calculates the following six feature quantities on the basis of a magnitude of motion of the motion region. The second calculating part 130 associates the six calculated feature quantities and identification information of the region, and outputs the associated feature quantities and identification information to the identifying part 140.

(1) A "maximum value of a magnitude of motion" is a maximum value of a magnitude of motion of each motion region. The second calculating part 130 calculates the "maximum value of the magnitude of the motion" according to the following Formula (1). In the formula, "t" represents time, that is, a value of a frame of a time-series image, and "D(t)" represents a value of a magnitude of motion. For example, when a magnitude of motion of a certain motion region is designated as D(1) to D(59) for each frame, the "maximum value of the magnitude of the motion" is a largest value among D(1) to D(59). It is possible to appropriately exclude a motion region in which motion is extremely small other than myocardial cells, etc. by obtaining the maximum value of the magnitude of the motion as the feature quantity.

[Formula 1]

$$(\text{Maximum value of magnitude of motion}) = \max(D(t)) \quad (1)$$

(2) A "degree of projection" is a maximum value of a ratio of change (hereinafter referred to as a "rate of change") in the magnitude of the motion calculated while a reference frame changes. The rate of change is a value calculated on the basis of a comparison between a sum of magnitudes of motions in a predetermined number of frames before a focused reference frame and a sum of magnitudes of motions in a predetermined number of frames after the reference frame for each motion region. Accordingly, when values of magnitudes of motions in a predetermined number of frames before the reference frame are small and values of magnitudes of motions in a predetermined number of frames after the reference frame are large, the rate of change becomes a large value. On the other hand, the rate of change does not increase if magnitudes of motions in a predetermined number of frames before the reference frame are large even when magnitudes of motions in a predetermined number of frames before the reference frame are large. Hereinafter, the above-described "predetermined number" is referred to as a window size. The second calculating part 130 calculates, for example, the "degree of projection" according to Formula (2). In Formula (2), w denotes a window size.

[Formula 2]

$$(\text{Degree of protection}) = \max_i \left( \frac{\sum_{t=i}^{i+w} D(t)}{\sum_{t=i-w}^{i} D(t)} \right) \quad (2)$$

When the degree of projection is calculated for magnitudes D(1) to D(59) of motions of a certain motion region, the second calculating part 130 first designates a sixth frame as a reference frame if the window size w is 5. The second calculating part 130 calculates a sum of magnitudes D(1) to D(6) of the motions from a first frame which is located five frames before the reference frame to the reference frame. Also, the second calculating part 130 calculates a sum of magnitudes D(6) to D(11) of motions from the reference frame to an eleventh frame which is located five frames after the reference frame.

The second calculating part 130 calculates the rate of change on the basis of a comparison between the calculated sum of the magnitudes D(6) to D(11) of the motions and the calculated sum of the magnitudes D(1) to D(6) of the motions (for example, by dividing the sum of D(6) to D(11) by the sum of D(1) to D(6)). The second calculating part 130 calculates, for example, the rate of change until a $54^{th}$ frame as a reference while the reference frame changes in order, for example, so that a sixth frame is the reference frame in the first time and a seventh frame is the reference frame in the second time. The degree of projection is a maximum value among calculated rates of change while the reference frame changes for each motion region.

Figure 8:
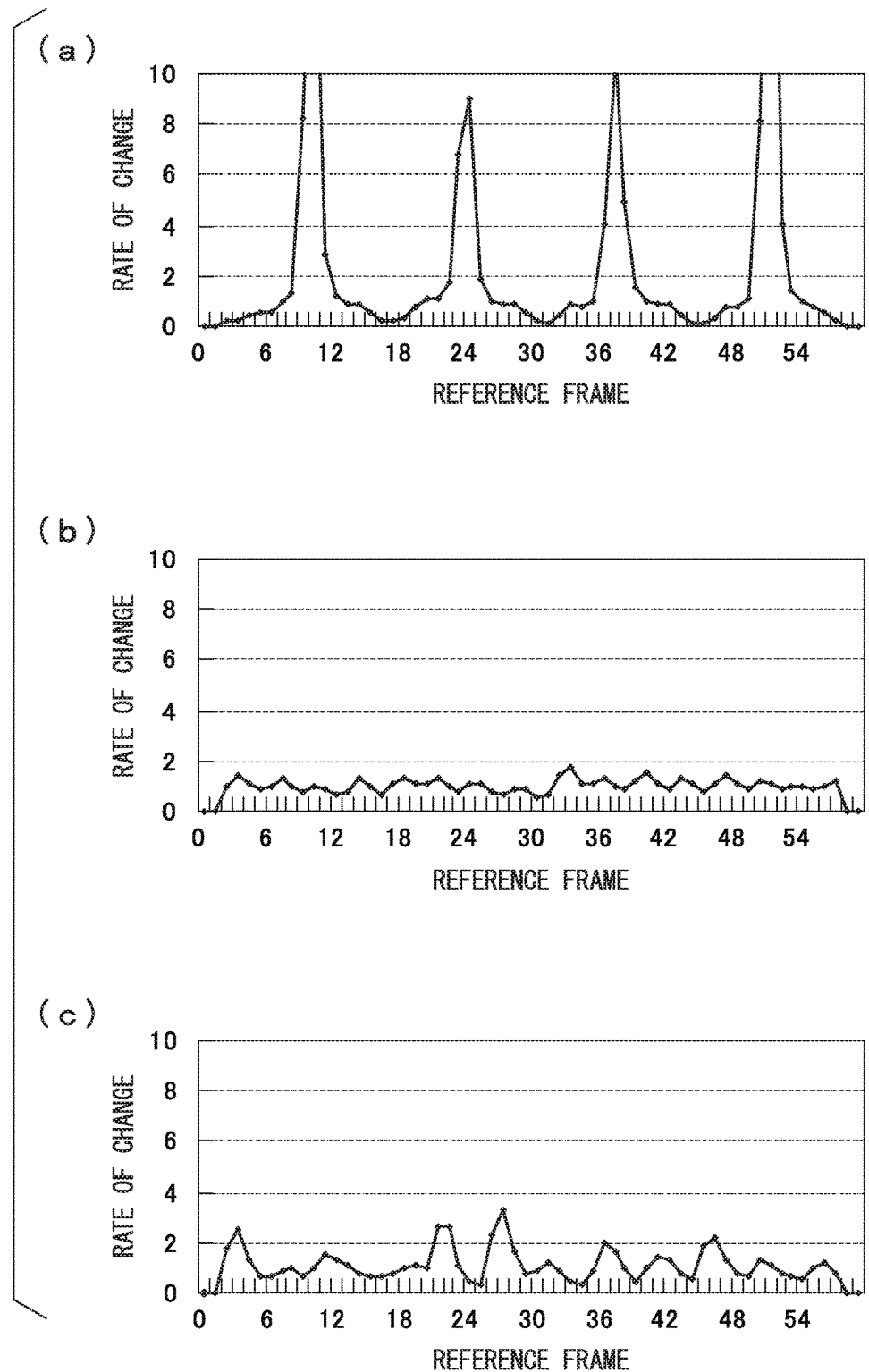
FIG. 8 is an example of a graph illustrating a change in a rate of change of the magnitude of the motion of each motion region.

FIG. 8 is an example of a graph illustrating a change in a rate of change of the magnitude of the motion of each motion region. The horizontal axis of the above-described graph represents a reference frame and the vertical axis of the above-described graph represents the rate of change. Also, in FIG. 8, (a) illustrates a pulsation region, (b) illustrates a shaking-of-liquid region, and (c) illustrates a noise region.

Because the relaxation (stationary state) and the contraction (motion state) are included in the pulsations of myocardial cells, the rate of change in the magnitude of the motion increases at the time of transition from the stationary state to the motion state. Accordingly, in the graph of the rate of change in the magnitude of the motion of the pulsation region, the stationary state is particularly lengthened to a certain extent (for example, about five or more frames) and then the rate of change significantly increases to show a clear peak as illustrated in FIG. 8(a).

On the other hand, in the motion region in which there is substantially no stationary state such as the shaking-of-liquid region, the rate of change in the magnitude of the motion does not increase. Accordingly, the graph of the rate of change in the magnitude of the motion of the shaking-of-liquid region does not show a clear peak as illustrated in FIG. 8(b).

Also, because a stationary state is possible but continuous motion is not much in a time of five frames of a window size in the noise region, the rate of change in the magnitude of the motion is small. Accordingly, the graph of the rate of change in the magnitude of the motion of the noise region does not show a clear peak as illustrated in FIG. 8(c).

As described above, the degree of projection is a feature quantity effective in identification of the pulsation region in which the stationary state clearly appears. Also, the degree of projection is an effective feature quantity for identifying myocardial cells in which periodicity is unable to be confirmed in an observation condition in this embodiment because there is only one contraction for a relatively long time (for example, four seconds or the like).

Here, it is possible to effectively detect the pulsation of myocardial cells by setting the window size to 3, 4, or more frames when a time distribution required for one pulsation of myocardial cells approximately fits within about 5 to 10 frames. The term "approximately fits" indicates that about 90[%] fit, about −2σ to +1σ fit in a normal distribution, and the distribution is defined in another standard. On the other hand, it is possible to enhance the effect of a filter in which the degree of projection of a region in which periodic motion is performed in a short cycle is evaluated to be low by setting the window size to be large to a certain extent. In order to improve the effect of the filter, for example, the window size may be set to about 10 frames. In order to achieve both detection sensitivity and the filter effect, it is desirable that the window size be set in a range from approximately ½ of a lower limit value to an upper limit value of a range (5 to 10 frames) in which a time distribution required for one pulsation of myocardial cells is included. In this embodiment, the window size is set to 5 frames as an example. Thereby, the image analyzing part 100 can more accurately extract the pulsations of myocardial cells without omission.

Also, the calculation formula of the degree of projection is not limited to Formula (2). For example, in Formula (2), a position of division is replaced with subtraction and an absolute value of a subtraction result may be calculated. As described above, the calculation of the degree of projection is not limited to a specific formula or method and it is only necessary to reflect a degree of change in a magnitude of motion.

(3) The "time periodicity" is, for example, a maximum value of an auto-correlation of a magnitude of motion calculated while a window interval changes. The second calculating part 130 calculates the "time periodicity" according to the following Formula (3). In the formula, τ denotes a window interval. Also, N denotes the total number of frames (for example, 59). The second calculating part 130 obtains an auto-correlation for each frame for each motion region and calculates a maximum value of the auto-correlation as the time periodicity.

[Formula 3]

$$(\text{Auto-correlation}) = \max_{\tau}\left(\frac{1}{N-\tau}\sum_{t=\tau}^{N} D(t)D(t-\tau)\right) \quad (3)$$

The calculation of the "time periodicity" by the second calculating part 130 will be described in further detail. For example, when the window interval τ is 1, the second calculating part 130 associates one-to-one magnitudes D(1) to D(58) of motions and magnitudes D(2) to D(59) of motions shifted by one frame.

The second calculating part 130 calculates products (D(1)×D(2), D(2)×D(3), . . . ) for sets of the associated magnitudes of the motions. Next, the second calculating part 130 calculates an average value of the calculated products. The calculated product is a large value when all the magnitudes of the motions associated as a set are large. Also, when an original magnitude of motion and a magnitude of motion shifted by a window interval are similar in all sets which change in each frame of a magnitude of motion, the auto-correlation increases because the calculated value is the average value. The second calculating part 130 changes, for example, the window interval in order so that the window interval is one frame in the first time and two frames in the second time, and calculates the auto-correlation when the frame is shifted until 58 frames. For each motion region, the "time periodicity" is a maximum value of the auto-correlation calculated for each frame. Accordingly, when the magnitude of the motion has periodicity, the "time periodicity" is a large value. In contrast, when the magnitude of the motion lacks periodicity, the "time periodicity" is a small value.

Figure 9:
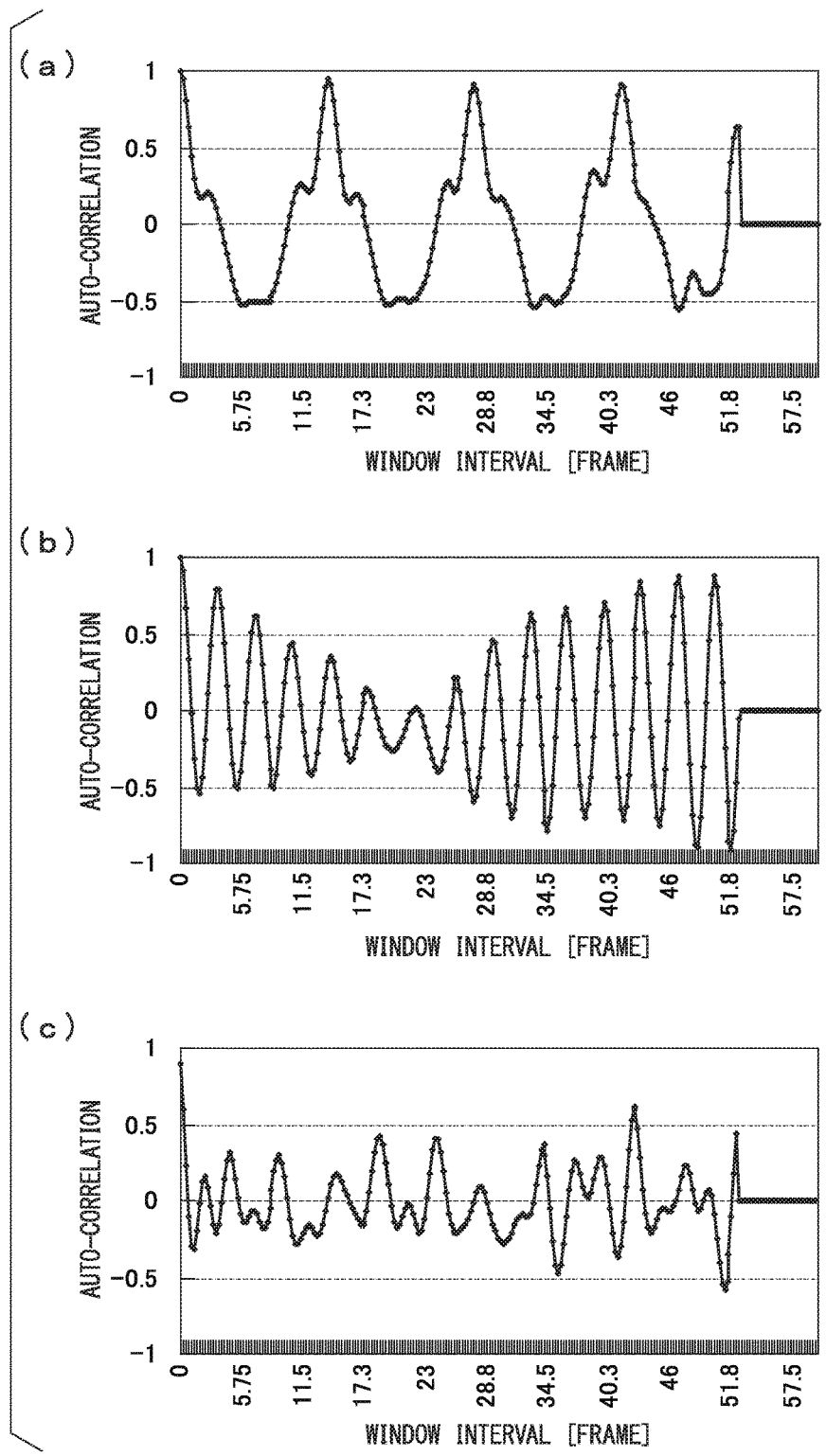
FIG. 9 is an example of a graph illustrating a change in an auto-correlation of the magnitude of the motion of each motion region.

FIG. 9 is an example of a graph illustrating a change in an auto-correlation of the magnitude of the motion of each motion region. The horizontal axis of the above-described graph represents a window interval τ of the time-series image and the vertical axis of the above-described graph represents the auto-correlation. Also, in FIG. 9, (a) illustrates a pulsation region, (b) illustrates a shaking-of-liquid region, and (c) illustrates a noise region. As described above, the motion of the pulsation region or the shaking-of-liquid region has a certain degree of periodicity. Thus, as illustrated in FIGS. 9(a) and 9(b), the auto-correlation of the pulsation region or the shaking-of-liquid region shows a peak according to a change in the window interval. On the other hand, because the motion of the noise region is aperiodic, the auto-correlation of the noise region does not show a clear peak as illustrated in FIG. 9(c). Accordingly, the "time periodicity" is an effective feature quantity for appropriately excluding the noise region.

Figure 10:
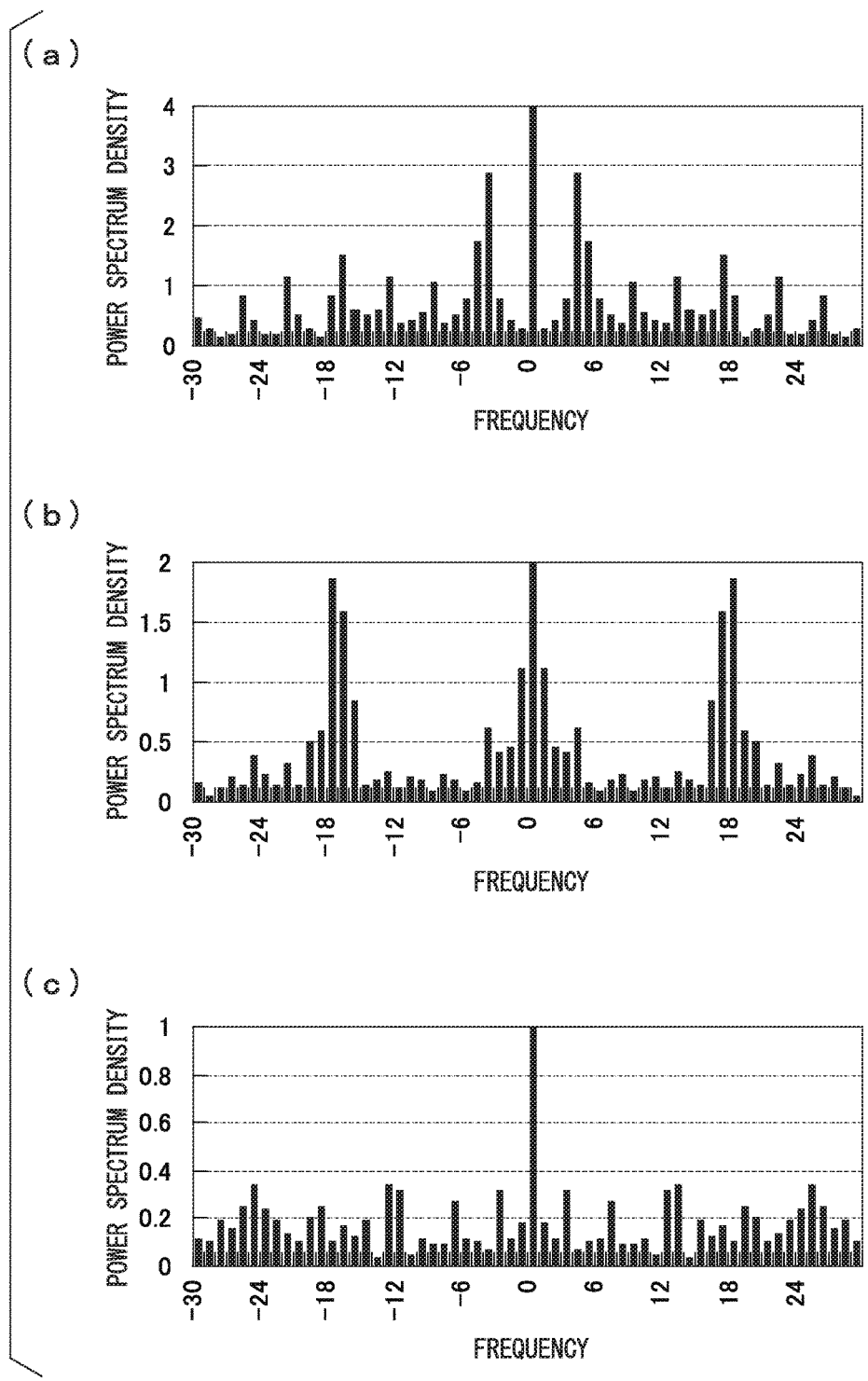
FIG. 10 is an example of a graph illustrating an example of a frequency spectrum of the magnitude of the motion of each motion region.

The remaining three feature quantities ((4) to (6)) are calculated from frequency spectra of magnitudes of motions. The second calculating part 130 calculates the frequency spectrum of the magnitude of the motion, for example, according to a Fourier transform. Because the calculation of the frequency spectrum according to the Fourier transform is well-known technology, a description thereof will be omitted here. The second calculating part 130 classifies a frequency component of the calculated magnitude of the motion into a high-frequency component, an intermediate-frequency component, and a low-frequency component. In the observation condition of this embodiment, the "high-frequency component" is, for example, a frequency component of a frequency of 15 to 29 [Hz], the "intermediate-frequency component" is, for example, a frequency component of a frequency of 7 to 12 [Hz], and the "low-frequency component" is, for example, a frequency component of a frequency of 1 to 6 [Hz]. FIG. 10 is an example of a graph illustrating an example of a frequency spectrum of the magnitude of the motion of each motion region. The horizontal axis of the above-described graph represents a frequency and the vertical axis of the above-described graph represents a power spectrum density. Also, in FIG. 10, (a) illustrates a pulsation region, (b) illustrates a shaking-of-liquid region, and (c) illustrates a noise region.

(4) A "high/low-frequency component ratio" is a ratio of a high-frequency component to a low-frequency component of a magnitude of motion. As illustrated in FIGS. 10(*a*) and 10(*b*), the number of high-frequency components of the magnitude of the motion of the shaking-of-liquid region is large compared to that of the magnitude of the motion of the pulsation region. Accordingly, the "high/low-frequency component ratio" is an effective feature quantity for identifying the pulsation region and the shaking-of-liquid region.

(5) An "intermediate/low-frequency component ratio" is a ratio of an intermediate-frequency component to a low-frequency component of a magnitude of motion. As illustrated in FIGS. 10(*a*) and 10(*b*), the number of intermediate-frequency components of the magnitude of the motion of the pulsation region is large compared to that of the magnitude of the motion of the shaking-of-liquid region. Accordingly, the "intermediate/low-frequency component ratio" is an effective feature quantity for identifying the pulsation region and the shaking-of-liquid region.

Also, the classification of the frequency component is not limited to the above-described classification. The second calculating part 130 may more finely classify the frequency component and may classify the frequency component into two types without classifying the frequency component into three types. Also, the above-described "high/low-frequency component ratio" and "intermediate/low-frequency component ratio" are an example of the feature quantity based on the frequency spectrum. The second calculating part 130 may calculate, for example, a power spectrum density of the high-frequency component or the intermediate-frequency component, a normalized power spectrum density obtained by normalizing the power spectrum density for any criterion, or a value obtained by applying a calculation operation to the power spectrum density and the normalized power spectrum density as the feature quantity.

(6) "Variance of the frequency spectrum" is the variance of the frequency component of the magnitude of the motion. As described above, the magnitudes of the motions of the pulsation region and the shaking-of-liquid region are periodic. Thus, variances of the frequency spectra of the pulsation region and the shaking-of-liquid region are reduced. On the other hand, as described above, the magnitude of the motion of the noise region is aperiodic. Thus, the frequency spectrum of the noise region does not show a specific peak and the variance of the frequency spectrum increases. Accordingly, the "variance of the frequency spectrum" is an effective feature quantity for appropriately excluding the noise region.

Also, the second calculating part 130 may calculate a feature quantity other than the above-described six feature quantities. For example, the luminance of the region may be an effective index in the identification of cells. This is because the luminance of a cell region is less than that of the shaking-of-liquid region or the noise region in many cases. As described above, the second calculating part 130 may calculate various feature quantities other than the above-described feature quantities on the basis of the magnitude of the motion of the motion region or a region-specific value.

[Identification of Type of Motion Region]

Hereinafter, a method of identifying the motion region will be described in detail. The identifying part 140 classifies each motion region into any one of the pulsation region, the shaking-of-liquid region, and the noise region on the basis of the feature quantity calculated by the second calculating part 130. In the method of identifying the motion region, for example, a k-proximity method can be used. When identification using the k-proximity method is performed, the image analyzing part 100 performs identification using teacher data pre-stored in the storage 150.

First, the identifying part 140 detects teacher data in which a distance on a coordinate space in which each feature quantity serves as a coordinate axis is close to data of a motion region of an unknown classification on the basis of a feature quantity calculated by the second calculating part 130 in a motion region of the unknown classification, wherein the number of pieces of the teacher data is a desired number k. The identifying part 140 determines that the type of most regions is that of a motion region of an unknown classification among types of regions of the k pieces of the teacher data. The identifying part 140 associates identification information of a motion region and an identified type of motion region, and stores the associated identification information and identified type in the storage 150. Thereafter, the information stored in the storage 150 may be used or not used as teacher data. The identifying part 140 is not limited to the k-proximity method and may identify a motion region using a technique such as a support and vector machine, discriminant analysis, or a decision tree.

Figure 11:
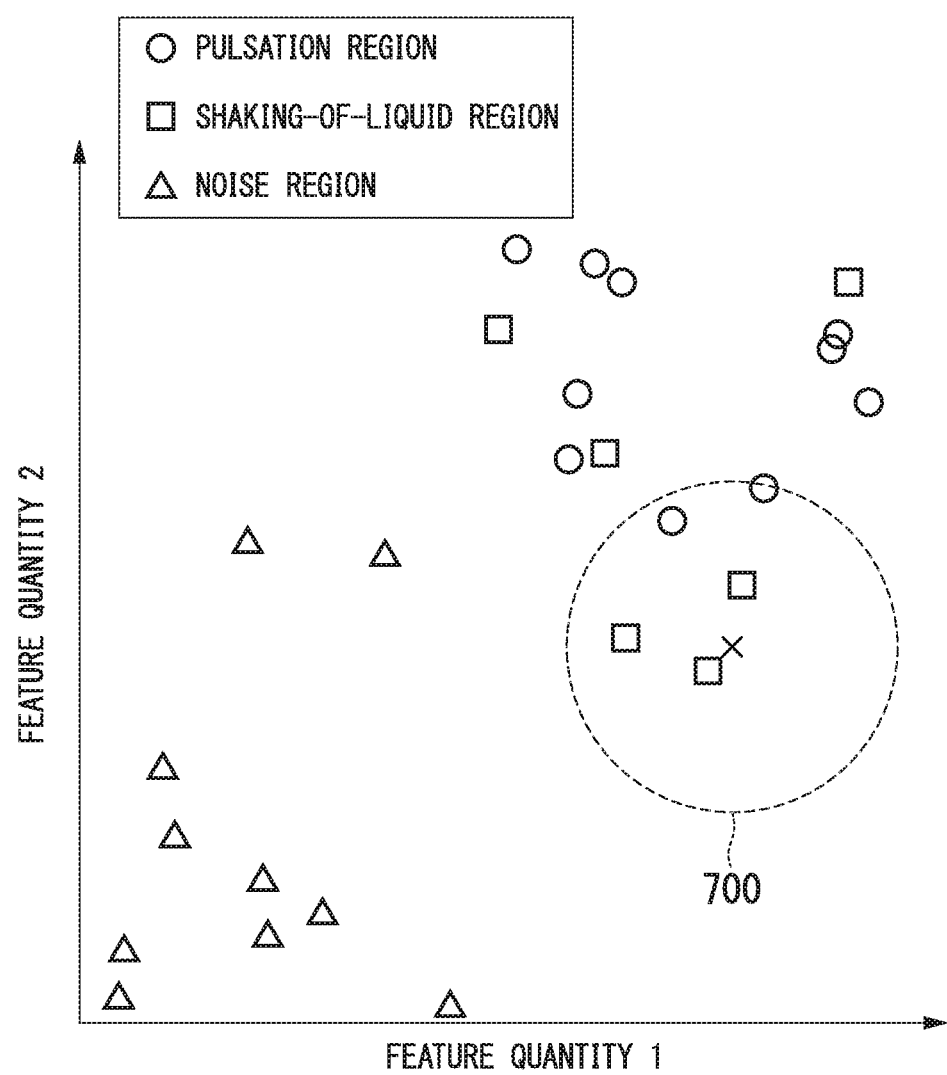
FIG. 11 is a diagram illustrating a technique in which an identifying part identifies a type of motion region.

FIG. 11 is a diagram illustrating a technique in which the identifying part 140 identifies a type of motion region.

Although the identifying part 140 identifies a type of motion region using the six feature quantities in this embodiment, FIG. 11 illustrates the case in which two feature quantities are simply used. In FIG. 11, the horizontal axis represents feature quantity 1 and the vertical axis represents feature quantity 2. In FIG. 11, teacher data of each type of motion region is plotted. The "○" symbol plotted in FIG. 11 denotes teacher data of a pulsation region, the "□" symbol denotes teacher data of the shaking-of-liquid region, and "Δ" denotes teacher data of the noise region. The "×" symbol is a motion region of an unknown classification extracted by the region extracting part 120, and is plotted at a corresponding position of FIG. 11 on the basis of the feature quantity calculated by the second calculating part 130.

In the k-proximity method, the identification of an unknown type of data is performed on the basis of a comparison with adjacent teacher data. Here, the case of k=5 will be described. In this case, the identifying part 140 compares data of an unknown type of region with five pieces of data adjacent to the data of the unknown type of region. Five pieces of data adjacent to data "×" of the unknown type of region are included in a circular region 700 around "×" of FIG. 11. A region of three pieces of the data among the five pieces of the data adjacent to "×" is the shaking-of-liquid region and a region of the remaining two pieces of the data is the pulsation region. Accordingly, the identifying part 140 determines that the region of the unknown classification indicating "×" is the shaking-of-liquid region from the majority of the types of the five adjacent regions.

[Conclusion]

As described above, according to the image analyzing part 100 of the first embodiment, because the second calculating part 130 calculates a feature quantity on the basis of a magnitude of motion of each motion region calculated by the region extracting part 120 and the identifying part 140 identifies whether the motion region is the pulsation region on the basis of the feature quantity calculated by the second calculating part 130, it is possible to more accurately identify the pulsation region (that is, a motion region in which autonomous motion is performed=an image element).

Also, according to the image analyzing part 100 of the first embodiment, because the second calculating part 130 calculates a plurality of feature quantities and the identifying part 140 identifies whether the motion region is the pulsation region on the basis of the plurality of feature quantities, it is possible to more accurately identify the pulsation region even when identification is difficult with only one feature quantity.

Also, according to the image analyzing part 100 of the first embodiment, because the second calculating part 130 calculates a degree of projection on the basis of a comparison of magnitudes of motions between two window sizes (time zones) which are temporally successive and the identifying part 140 identifies whether the motion region is the pulsation region on the basis of the degree of projection, it is possible to accurately identify pulsation region in which pulsation is not performed at an excessively high frequency. Also, according to the image analyzing part 100 of the first embodiment, because the second calculating part 130 calculates the degree of projection using a time from approximately ½ of a lower limit value to an upper limit value of a time (5 to 10 frames) in which a distribution of a time required for one pulsation of myocardial cells as the window size, it is possible to more accurately identify the pulsation region.

Also, according to the image analyzing part 100 of the first embodiment, because the second calculating part 130 calculates a feature quantity on the basis of a frequency spectrum of a magnitude of motion and the identifying part 140 identifies whether the motion region is the pulsation region using the feature quantity, it is possible to accurately identify a motion region different in a frequency characteristic. Also, the motion region identified to be the pulsation region, for example, may be indicated by a color such as a red color and displayed on a display part. Also, the motion region may be clearly displayed by surrounding the identified motion region by a line.

Also, a culturing method of further only culturing cells automatically extracted by a manipulator within the incubator is also provided. Thereby, it is possible to continue the culturing of only more select desired cells and provide effective cells in research of regenerative medicine and drug discovery.

Further, particularly in the field of drug discovery, an adding means such as a pipette for adding medicines serving as a research target to desired cells cultured by the continued culture may be provided. It is also possible to further continue the research of drug discovery using the continuously cultured cells by providing the adding means. The adding means may be arranged outside the incubator in consideration of a problem of contamination (a mixing of bacteria or the like) by a diffusion of added medicines into the incubator. In this case, it is preferable to provide a conveying device configured to convey a culturing container in which cells are stored between the incubator and the device provided with the adding means.

According to this configuration, a state of the cells to which the medicines are added can be observed and analysis by an image is also possible.

Also, the incubator 10 may be configured as a cell manufacturing device including a manipulator (an acquiring part) configured to automatically extract cells of a part identified to be the pulsation region. The same is true even in second to fourth embodiments to be described below.

Second Embodiment

<Configuration>

Figure 12:
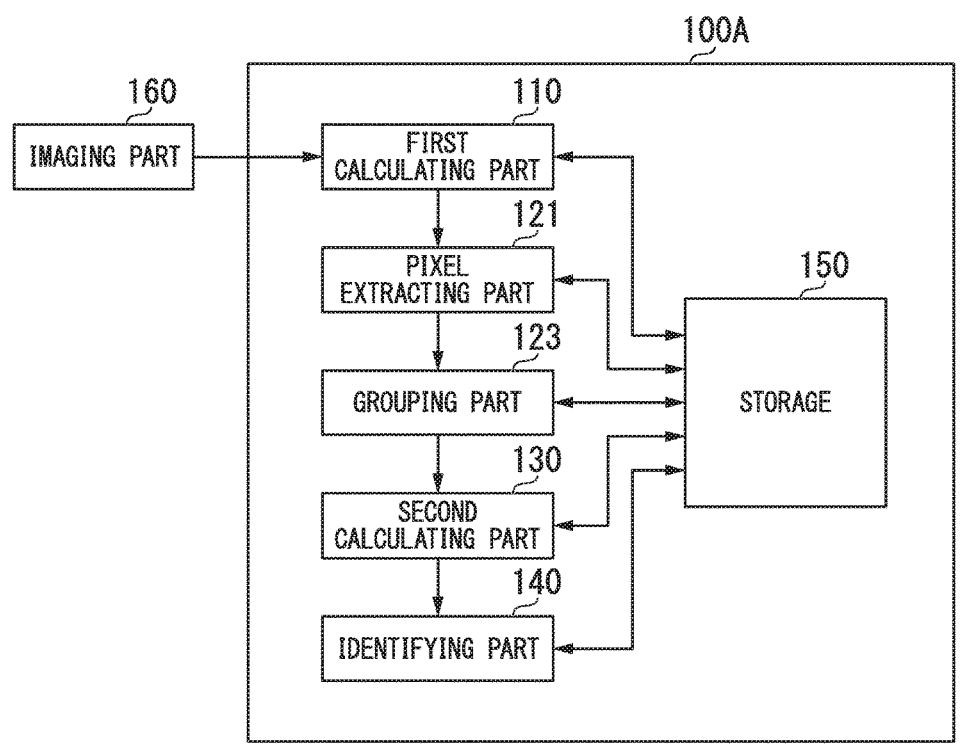
FIG. 12 is a diagram illustrating an example of a functional configuration of an image analyzing part according to a second embodiment.

Hereinafter, an image analyzing part (an image analysis device) according to the second embodiment will be described. Description of components similar to those of the first embodiment will be omitted. FIG. 12 is a diagram illustrating an example of a functional configuration of an image analyzing part 100A according to the second embodiment. As in the first embodiment, the image analyzing part 100A is one functional part of a controller 50 of an incubator 10 or is implemented by a computer independent from the incubator 10. The image analyzing part 100A includes, for example, a first calculating part 110, a pixel extracting part 121, a grouping part 123, a second calculating part 130, an identifying part 140, and a storage 150. These functional parts are, for example, software function parts which function by executing a program stored in the storage 150 by the CPU of the controller 50. Also, some or all of these functional parts may be hardware function parts such as LSI and an ASIC.

As in the first embodiment, the first calculating part 110 calculates a magnitude of motion for each pixel of an image. Similar to the region extracting part 120 of the first embodiment, the pixel extracting part 121 extracts a pixel of large motion on the basis of the magnitude of the motion of each pixel for each time-series image and causes the storage 150 to store the extracted pixel. That is, the pixel extracting part 121 performs the processes of steps S500 to S506 in the flowchart of FIG. 5.

The grouping part 123 groups pixels similar in magnitude of motion (which is an example of the feature quantity related to the motion) between "pixels having large magnitudes of motions" extracted by the pixel extracting part 121 as candidates for pixels of one group obtained by imaging the same myocardial cell. The pixels grouped by the grouping part 123 are handled the same as the "motion region" in the first embodiment. That is, the grouping part 123 extracts a pixel ("a pixel having largest motion within the region") in which a magnitude of largest motion is shown among pixels within each group (motion region), selects an image region of 5×5 pixels around the pixel having the largest motion within the region, and calculates an average value of magnitudes of motions of the selected image region of 5×5 pixels for all the time-series images. The grouping part 123 outputs the calculated magnitude of the motion of each motion region to the second calculating part 130 with identification information of the corresponding motion region.

Hereinafter, a grouping process will be described. The grouping part 123 extracts, for example, some pixels (hereinafter referred to as "representative pixels") in which motion is particularly large from the pixels extracted by the pixel extracting part 121. The term "particularly large," for example, indicates that the magnitude of the motion is greater than or equal to a second threshold value greater than the threshold value used during extraction by the pixel extracting part 121. Also, in place of this, for example, a pixel in which the magnitude of the motion is about several [%] of the higher order may be designated as a representative pixel. The grouping part 123 calculates degrees of similarity for combinations of representative pixels and all other pixels, and includes the representative pixels and the other pixels in the same group when the degree of similarity, for example, is greater than or equal to the threshold value. Also, the grouping part 123 may include representative pixels in the same group.

[Degree of Similarity]

The degree of similarity, for example, is calculated according to a normalization cross-correlation represented by Formula (4). In Formula (4), D(t) denotes a magnitude of motion, over-line D denotes an average value of magnitudes of motions, and N denotes the total number of frames (for example, 59). Thereby, an extent to which a change in a magnitude D(t) of motion is similar can be appropriately converted into a numerical value.

[Formula 4]

$$(\text{Degree of similarity}) = \frac{\sum_{t=0}^{N}(D_1(t) - \overline{D_1})(D_2(t) - \overline{D_2})}{\sqrt{\sum_{t=0}^{N}(D_1(t) - \overline{D_1})^2}\sqrt{\sum_{t=0}^{N}(D_2(t) - \overline{D_2})^2}} \quad (4)$$

Also, the grouping part 123 may calculate a degree of similarity of a pixel at a large distance as a small value while reflecting a distance between pixels in the calculation of the degree of similarity. In this case, the grouping part 123 may calculate the degree of similarity by multiplying an index value of a normalization cross-correlation or the like by a reciprocal of the distance or a reciprocal of the square of the distance. Formula (5) indicates a degree of similarity obtained by multiplying the reciprocal of the distance by the normalization cross-correlation. In Formula (5), $X_{12}$ denotes a distance between pixel 1 and pixel 2. Pixels which are distant and which have a similar cycle of motion can be prevented from being unintentionally included in the same group.

[Formula 5]

$$(\text{Degree of similarity}) = \frac{1}{X_{12}} \times \frac{\sum_{t=0}^{N}(D_1(t) - \overline{D_1})(D_2(t) - \overline{D_2})}{\sqrt{\sum_{t=0}^{N}(D_1(t) - \overline{D_1})^2}\sqrt{\sum_{t=0}^{N}(D_2(t) - \overline{D_2})^2}} \quad (5)$$

As described above, it is possible to more appropriately segment a motion region by designating one group of pixels grouped on the basis of a degree of similarity as a motion region. Here, in the first embodiment, mutually adjacent pixels among pixels determined to have large magnitudes of motion are designated as one group of pixels, that is, a motion region. On the other hand, the myocardial pulsation has a unique cycle and moves in the same cycle in pixels obtained by imaging the same myocardial cell. Also, when there is a part of small motion among myocardial cells, one myocardial cell may be imaged across mutually separated pixels as a result of determining that "motion is small" in the part by the pixel extracting part 121.

Figure 13:
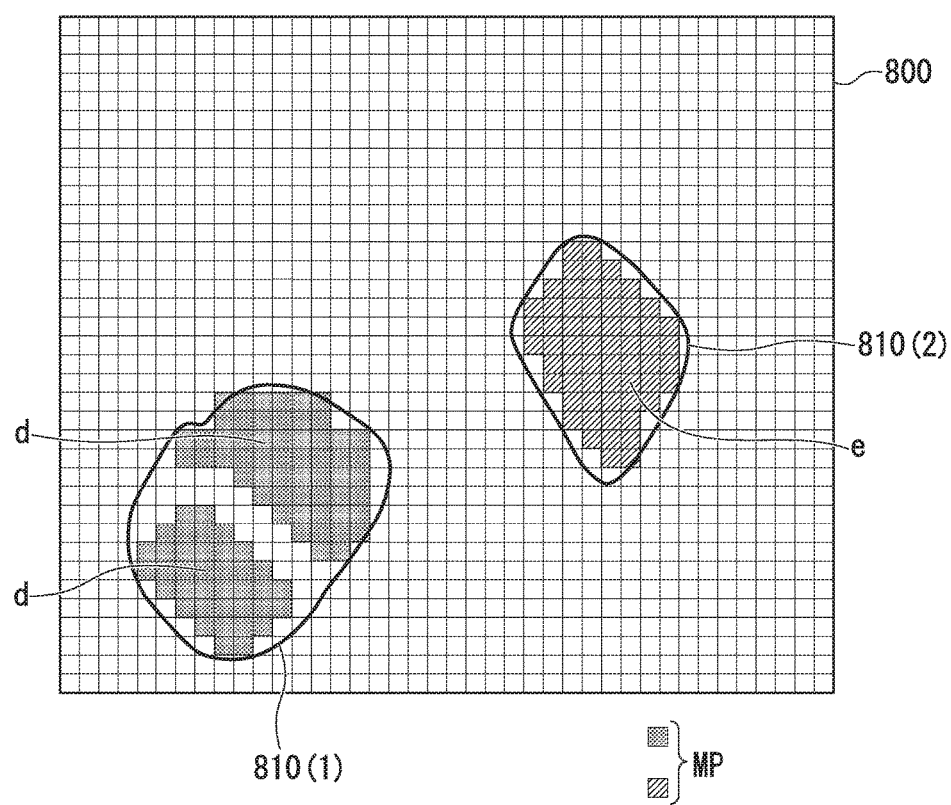
FIG. 13 is a diagram illustrating an example of myocardial cells included in a part of an image captured by an imaging part, pixels for which a pixel extracting part determines that "the motion is large," and a motion region extracted by a grouping part.

Accordingly, in the image analyzing part 100A of the second embodiment, it is possible to extract pixels for which motion is performed in the same cycle by extracting a magnitude of motion as a one-dimensional signal of time series for each pixel and calculating a degree of similarity between pixels on the basis of the one-dimensional signal because a plurality of pixels for which motion is performed in the same cycle are handled as one motion region. As a result, the image analyzing part 100A of the second embodiment can reduce a possibility of handling pixels which should originally belong to one pulsation region as a separate motion region or conversely handling two pulsation regions as one motion region. FIG. 13 is a diagram illustrating an example of myocardial cells 810(1) and 810(2) included in a part 800 of an image captured by the imaging part 160, pixels MP for which it is determined that "motion is large" by the pixel extracting part 121, and motion regions d and e extracted by the grouping part 123. As illustrated, pixels MP for which it is determined that "motion is large" by the pixel extracting part 121 may appear as pixel groups separated from each other even when the same myocardial cell 810 is imaged. In the image analyzing part 100A of the second embodiment, it is possible to include pixels obtained by imaging the same myocardial cell in the same motion region even in this case.

When the motion region is determined by the grouping part 123, the second calculating part 130 and the identifying part 140 execute a similar process to the first embodiment. Description of the similar process will be omitted.

[Conclusion]

According to the image analyzing part 100A of the second embodiment described above, it is possible to more accurately group pixels of one group for which the same motion object (a myocardial cell) is likely to be imaged by including pixels similar in a change in a magnitude of motion in the same group.

Also, according to the image analyzing part 100A of the second embodiment, it is possible to prevent pixels for which the same myocardial cell is unlikely to be originally imaged from being included in the same group by calculating degrees of similarity of pixels at relatively large distances as small values.

Also, the grouping part 123 performs grouping on the basis of representative pixels in which motion is particularly large in the second embodiment. However, in place of this, degrees of similarity may be calculated for all combinations of pixels extracted by the pixel extracting part 121 and grouping may be performed. Also, the pixel extracting part 121 may be omitted and the grouping part 123 may calculate degrees of similarity to perform grouping for combinations of all pixels including pixels which are excluded due to small motion when the pixel extracting part 121 is present.

Third Embodiment

Figure 14:
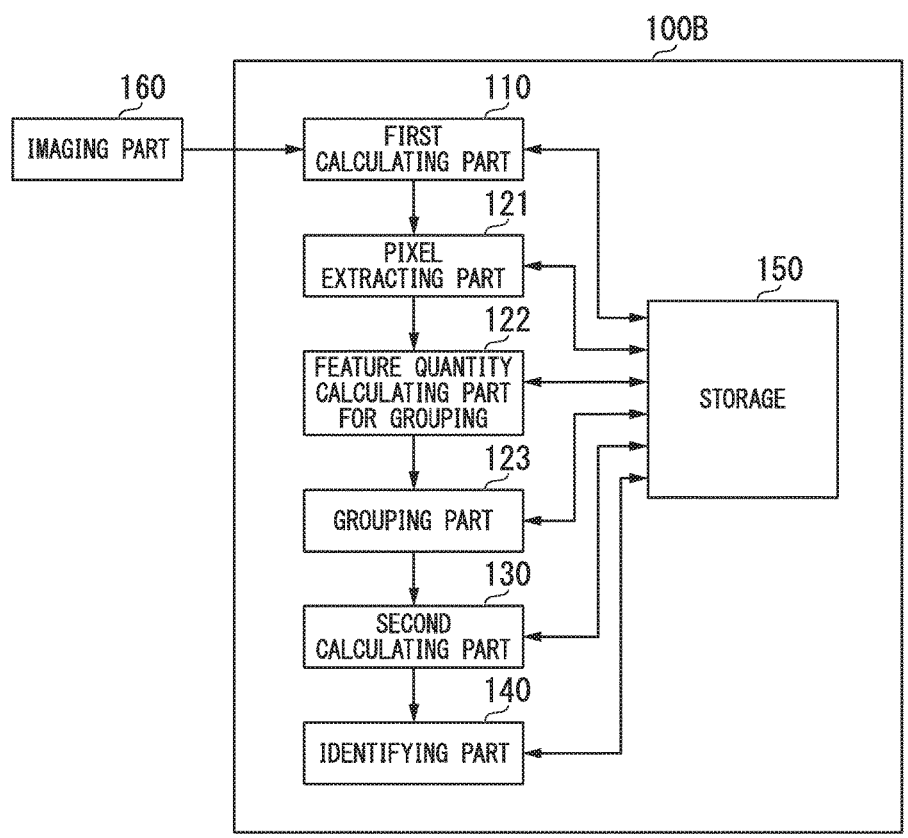
FIG. 14 is a diagram illustrating an example of a functional configuration of an image analyzing part according to a third embodiment.

Hereinafter, an image analyzing part (an image analysis device) according to the third embodiment will be described. Description of components similar to those of the first embodiment will be omitted. FIG. 14 is a diagram illustrating an example of a functional configuration of an image analyzing part 100B according to the third embodiment. As in the first embodiment, the image analyzing part 100B is one functional part of a controller 50 of an incubator 10 or is implemented by a computer independent from the incubator 10. The image analyzing part 100B includes, for example, a first calculating part 110, a pixel extracting part 121, a feature quantity calculating part 122 for grouping, a grouping part 123, a second calculating part 130, an identifying part 140, and a storage 150. These functional parts are, for example, software function parts which function by executing a program stored in the storage 150 by the CPU of the controller 50. Also, some or all of these functional parts may be hardware function parts such as LSI and an ASIC.

As in the first embodiment, the first calculating part 110 calculates a magnitude of motion for each pixel of an image. Similar to the region extracting part 120 of the first embodiment, the pixel extracting part 121 extracts a pixel of large motion on the basis of a magnitude of motion of each pixel for each time-series image and causes the storage 150 to store the extracted pixel. That is, the pixel extracting part 121 performs the processes of steps S500 to S506 in the flowchart of FIG. 5.

The feature quantity calculating part 122 for grouping calculates, for example, a plurality of feature quantities for pixels for which it is determined that "motion is large" by the pixel extracting part 121. The feature quantities calculated by the feature quantity calculating part 122 for the grouping are, for example, a rate of change (in parentheses of Formula (2)) in a magnitude of motion and a frequency component ratio of a magnitude of motion described in the first embodiment, etc.

For example, as in the second embodiment, the grouping part 123 according to the second embodiment extracts some representative pixels from pixels extracted by the pixel extracting part 121, performs clustering analysis according to a technique, for example, such as a mean shift, on a plurality of feature quantities between the representative pixels and all other pixels, and sets a pixel group belonging to the same group according to clustering in one motion region serving as pixels similar in a feature quantity. Here, the feature quantity may include both a magnitude of motion calculated by the first calculating part 110 and a feature quantity calculated by the feature quantity calculating part 122 for the grouping. Also, the grouping part 123 may include the representative pixels in the same group. Also, the grouping part 123 may obtain a normalization cross-correlation for a plurality of feature quantities to calculate a degree of similarity.

As described above, it is possible to more appropriately segment a motion region by setting a group of pixels grouped by performing clustering analysis on the basis of a plurality of feature quantities calculated for each pixel as a motion region. Because this is similar to the second embodiment, a description thereof will be described. Also, when the motion region is determined by the grouping part 123, the second calculating part 130 and the identifying part 140 executes a similar process to the first embodiment. Also, even in the third embodiment, as in the second embodiment, a process of reducing the possibility that pixels for which a relative distance is large belong to the same motion region may be performed.

[Conclusion]

According to the image analyzing part 100B of the third embodiment described above, it is possible to more accurately group pixels of one group for which the same motion object (a myocardial cell) is likely to be imaged by setting a group of pixels grouped by performing clustering analysis on the basis of a plurality of feature quantities calculated for each pixel as a motion region.

Also, the grouping part 123 performs grouping on the basis of representative pixels having particularly large motions in the third embodiment. However, in place of this, degrees of similarity may be calculated for all combinations of pixels extracted by the pixel extracting part 121 and grouping may be performed. Also, the pixel extracting part 121 may be omitted and the grouping part 123 may perform clustering analysis or calculation of degrees of similarity and grouping for combinations of all pixels including pixels which are excluded due to small motion when the pixel extracting part 121 is present.

Fourth Embodiment

Figure 15:
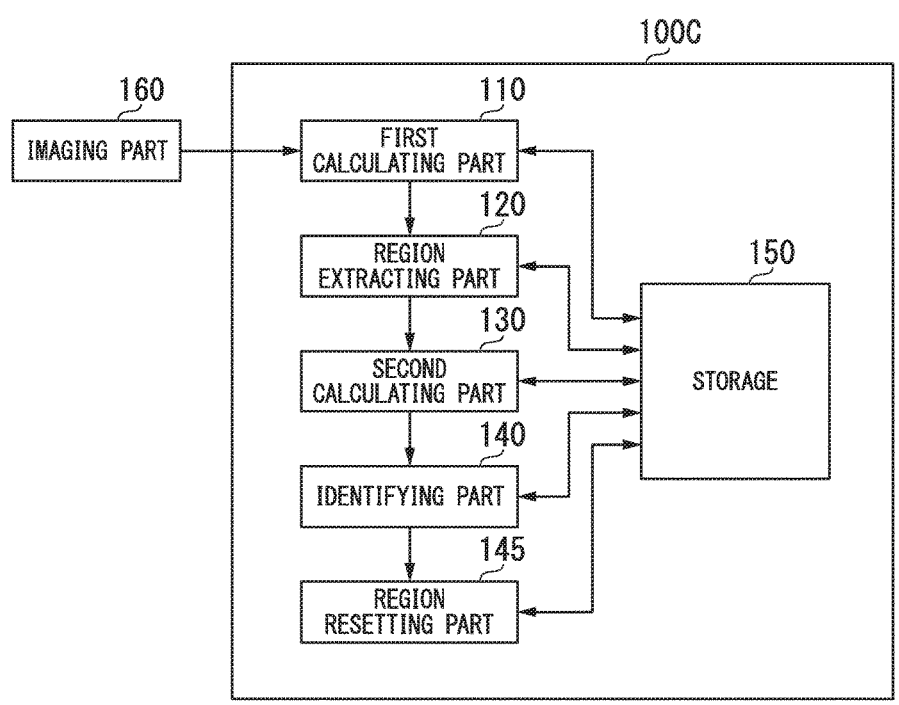
FIG. 15 is a diagram illustrating an example of a functional configuration of an image analyzing part according to a fourth embodiment.

Hereinafter, an image analyzing part (an image analysis device) according to the fourth embodiment will be described. Description of components similar to those of the first embodiment will be omitted. FIG. 15 is a diagram illustrating an example of a functional configuration of an image analyzing part 100c according to the fourth embodiment. As in the first embodiment, the image analyzing part 100C is one functional part of a controller 50 of an incubator 10 or is implemented by a computer independent from the incubator 10. The image analyzing part 100C includes, for example, a first calculating part 110, a region extracting part 120, a second calculating part 130, an identifying part 140, a region resetting part 145, and a storage 150. These functional parts are, for example, software function parts to function by executing a program stored in the storage 150 by the CPU of the controller 50. Also, some or all of these functional parts may be hardware function parts such as LSI and an ASIC. Because the first calculating part 110, the region extracting part 120, the second calculating part 130, and the identifying part 140 are similar to those of the first embodiment, a description thereof will be omitted.

Figure 16:
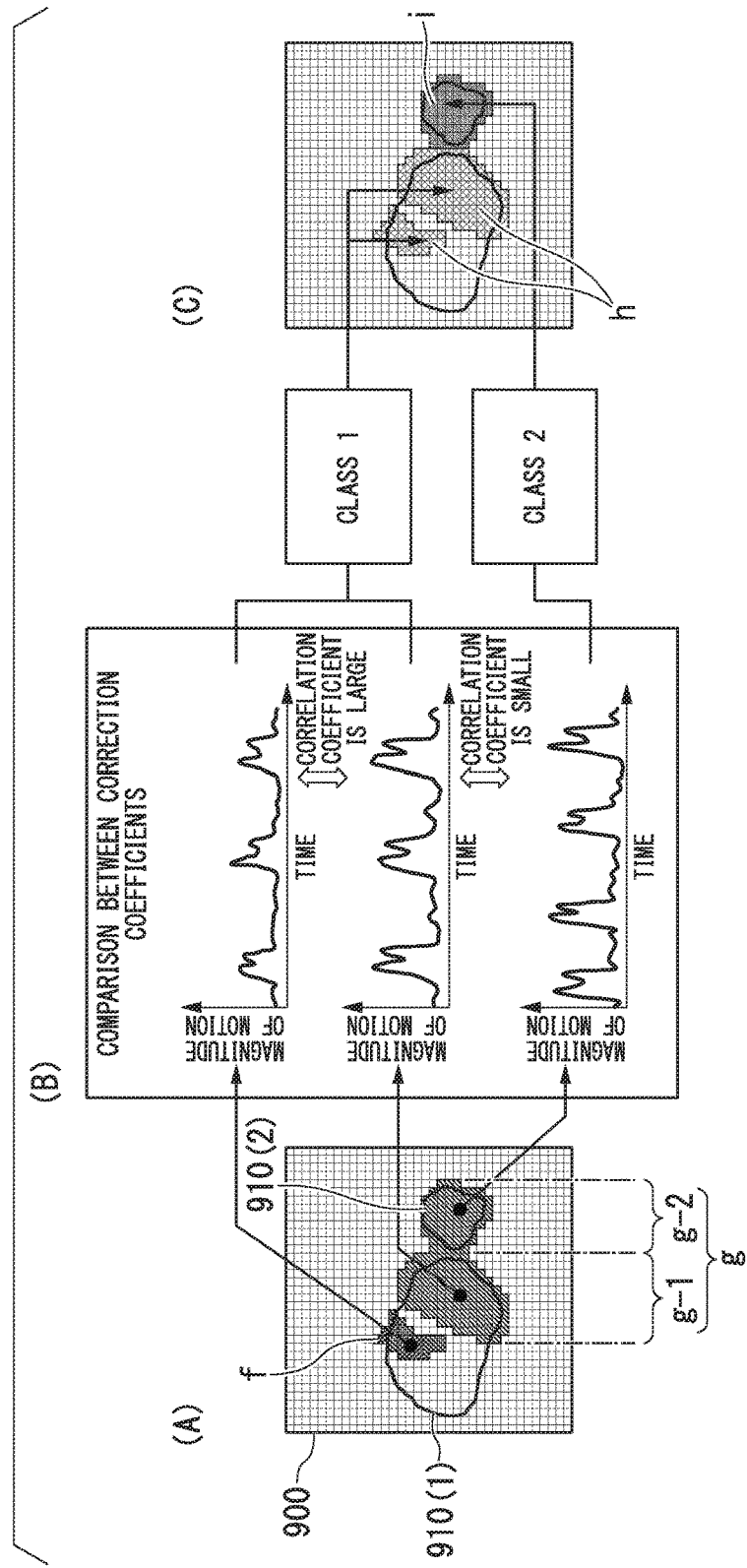
FIG. 16 is a diagram schematically illustrating an example of a flow of processing by a region resetting part.

The region resetting part 145 determines whether one motion region or a plurality of motion regions identified to be a pulsation region by the identifying part 140 are based on the same myocardial cell and resets the pulsation region. FIG. 16 is a diagram schematically illustrating an example of a flow of processing by the region resetting part 145. FIG. 16(A) illustrates myocardial cells 910(1) and 910(2) included in a part 900 of an image captured by the imaging part 160 and pulsation regions f and g identified to be pulsation regions by the identifying part 140. In FIG. 16(A), the pulsation regions f and g obtained by imaging the same myocardial cell 910(1) are output as separate pulsation regions by the parts from the first calculating part 110 to the identifying part 140. Also, the myocardial cell 910(2) separate from the myocardial cell (1) is included in the pulsation region g. The region resetting part 145 resets pulsation regions in view of the fact that such a situation may occur.

First, the region resetting part 145, for example, searches for a constriction position in a shape of the pulsation region and divides the pulsation region into a plurality of regions. The constriction region, for example, can be discovered by dividing a shape while a position and a tilt of a division line change and obtaining a division line by which a length is minimized. Also, in place of this, the region resetting part 145 may divide the pulsation region randomly (or in a lattice shape of a desired size). Also, the region resetting part 145 may not divide a small size pulsation region such as the pulsation region f illustrated in FIG. 16(A). Here, the pulsation region g is assumed to be divided into pulsation regions g-1 and g-2.

Next, the region resetting part 145, for example, calculates a magnitude of motion for each of the pulsation regions f, g-1, and g-2. The region resetting part 145 may calculate another feature quantity related to motion in place of or in addition to the magnitude of the motion. For example, as in the first embodiment, the magnitude of the motion of the pulsation region is obtained by selecting an image region of 5×5 pixels around the pixel having the largest motion within the region indicating a magnitude of largest motion among pixels within the pulsation region, and obtaining an average value of magnitudes of motions of the selected image region of 5×5 pixels.

Next, the region resetting part 145 calculates a degree of similarity, for example, by obtaining a correlation coefficient between magnitudes of motions calculated for the pulsation regions f, g-1, and g-2 (see FIG. 16(B)). Here, it is assumed that the correlation coefficient between the pulsation regions f and g-1 is calculated to be large, and the correlation coefficient between the pulsation regions g-1 and g-2 is calculated to be small. As a result, the region resetting part 145 newly resets the pulsation regions f and g-1 as one pulsation region h, and newly resets the pulsation region g-2 as one pulsation region i (see FIG. 16(C)). Thereby, the region resetting part 145 can more accurately group pixels of one group for which the same myocardial cell is likely to be imaged.

[Conclusion]

According to the image analyzing part 100C of the fourth embodiment described above, it is possible to more accurately group pixels of one group for which the same motion object (a myocardial cell) is likely to be imaged because it is determined whether one motion region or a plurality of motion regions identified to be a pulsation region by the identifying part 140 are based on the same myocardial cell and the pulsation region is reset.

Although embodiments of the present invention have been described above with reference to the drawings, specific configurations are not limited to the embodiments, and various design changes, etc. may also be included without departing from the scope of the present invention.

For example, a process of each embodiment described above may be performed on an observation target different from the myocardial cells.

Also, the function of the second or third embodiment and the function of the fourth embodiment may be combined. That is, pixels (or a motion region) in which a feature quantity related to motion is similar may be reset as a motion region of a processing target before the pulsation region is identified, and a region in which a feature quantity related to motion is similar may be reset as the pulsation region even after the pulsation region is identified.

REFERENCE SIGNS LIST

10 Incubator
19 Culturing container
20 Stocker
30 Container transporting part
40 Observation unit
50 Controller
100, 100A, 100B, 100C Image analyzing part
110 First calculating part
120 Region extracting part
121 Pixel extracting part
122 Feature quantity calculating part for grouping
123 Grouping part
130 Second calculating part
140 Identifying part
145 Region resetting part
150 Storage
160 Imaging part

The invention claimed is:

1. An image analysis device comprising a computer configured to operate as:
   a first calculating part that calculates a magnitude of motion of an image element from time-series images of pulsating myocardial cells;
   a second calculating part that calculates a feature quantity based on the magnitude of the motion of the image element calculated by the first calculating part; and
   an identifying part that identifies whether the image element is a predetermined image element based on the feature quantity calculated by the second calculating part, wherein
   the second calculating part calculates the feature quantity based on a comparison between magnitudes of motions of image elements in images of two time zones which are temporally successive among the time-series images.

2. The image analysis device according to claim 1,
   wherein the second calculating part calculates a plurality of feature quantities, and
   wherein the identifying part identifies whether the image element is the predetermined image element based on the plurality of feature quantities.

3. The image analysis device according to claim 1, wherein the second calculating part calculates the feature quantity using a time period from a value which is approximately ½ times a lower limit value to an upper limit value in a distribution of a time period required for one pulsation as a length of the time zone.

4. The image analysis device according to claim 1, wherein the second calculating part calculates a frequency spectrum of the magnitude of the motion of the image element and calculates the feature quantity based on the calculated frequency spectrum.

5. An image analysis method comprising:
   computing, by a computer, a magnitude of motion of an image element from time-series images of pulsating myocardial cells;
   computing, by the computer, a feature quantity based on the calculated magnitude of the motion of the image element; and
   identifying, by the computer, whether the image element is a predetermined image element based on the calculated feature quantity, wherein
   the computer calculates the feature quantity based on a comparison between magnitudes of motions of image elements in images of two time zones which are temporally successive among the time-series images.

6. A non-transitory computer-readable storage medium on which is stored an image analysis program that causes a computer to:
   calculate a magnitude of motion of an image element from time-series images of pulsating myocardial cells;
   calculate a feature quantity based on the calculated magnitude of the motion of the image element; and
   identify whether the image element is a predetermined image element based on the calculated feature quantity, wherein
   the feature quantity is calculated based on a comparison between magnitudes of motions of image elements in images of two time zones which are temporally successive among the time-series images.

* * * * *